US012029647B2

(12) United States Patent
Chambers et al.

(10) Patent No.: US 12,029,647 B2
(45) Date of Patent: Jul. 9, 2024

(54) SYSTEMS, METHODS AND DEVICES FOR PROSTHETIC HEART VALVE WITH SINGLE VALVE LEAFLET

(71) Applicant: 4C Medical Technologies, Inc., Brooklyn Park, MN (US)

(72) Inventors: Jeffrey W. Chambers, Maple Grove, MN (US); Saravana B. Kumar, Minnetonka, MN (US); Joseph P. Higgins, Minnetonka, MN (US); Robert J. Thatcher, Blaine, MN (US); Jason S. Diedering, Minneapolis, MN (US); Jeffrey R. Stone, Minnetonka, MN (US)

(73) Assignee: 4C Medical Technologies, Inc., Maple Grove, MN (US)

(*) Notice: Subject to any disclaimer, the term of this patent is extended or adjusted under 35 U.S.C. 154(b) by 0 days.

(21) Appl. No.: 15/913,509

(22) Filed: Mar. 6, 2018

(65) Prior Publication Data
US 2018/0256329 A1     Sep. 13, 2018

Related U.S. Application Data

(60) Provisional application No. 62/468,112, filed on Mar. 7, 2017.

(51) Int. Cl.
*A61F 2/24*        (2006.01)
(52) U.S. Cl.
CPC .......... *A61F 2/2445* (2013.01); *A61F 2/2409* (2013.01); *A61F 2/2463* (2013.01); *A61F 2220/0091* (2013.01)
(58) Field of Classification Search
CPC ........ A61F 2/24; A61F 2/2409; A61F 2/2445; A61F 2/2463
See application file for complete search history.

(56) References Cited

U.S. PATENT DOCUMENTS 4,424,833 A    1/1984   Spector
4,503,569 A    3/1985   Dotter
(Continued)

FOREIGN PATENT DOCUMENTS

AU    2014203064 B2    6/2015
AU    2015230879 A1    10/2015
(Continued)

OTHER PUBLICATIONS

Notification Concerning Transmittal of International Preliminary Report on Patentability (Chapter I of the Patent Cooperation Treaty) and International Preliminary Report on Patentability, issued Sep. 10, 2019, for PCT Application No. PCT/US2018/021244, filed Mar. 7, 2018.
(Continued)

*Primary Examiner* — Matthew W Schall
(74) *Attorney, Agent, or Firm* — Weiss & Arons LLP

(57) ABSTRACT

Devices and methods for supplementing and/or replacing native cardiac valve functionality, e.g., the mitral valve with a single prosthetic leaflet. An exemplary device is directed to dysfunctional mitral valves. In some cases, the entire device, including the single prosthetic leaflet, will be arranged entirely above the dysfunctional mitral valves and, therefore, disposed entirely within the left atrium. In other cases, the valve support and/or single prosthetic leaflet may extend a distance into the annulus between the left atrium and left ventricle. In some cases, the device will not physically interact with the native leaflets. In other cases, the device may physically interact with the native leaflets.

13 Claims, 7 Drawing Sheets

(56) References Cited

U.S. PATENT DOCUMENTS

| | | |
|---|---|---|
| 4,733,665 A | 3/1988 | Palmaz |
| 4,878,906 A | 11/1989 | Lindemann |
| 5,190,528 A | 3/1993 | Fonger |
| 5,415,667 A | 5/1995 | Frater |
| 5,441,483 A | 8/1995 | Avitall |
| 5,693,083 A | 12/1997 | Baker |
| 5,693,089 A | 12/1997 | Inoue |
| 5,776,188 A | 7/1998 | Shepherd |
| 5,843,090 A | 12/1998 | Schuetz |
| 5,928,258 A | 7/1999 | Khan |
| 5,957,949 A | 9/1999 | Leonhardt |
| 5,968,070 A | 10/1999 | Bley |
| 6,123,723 A | 9/2000 | Konya |
| 6,152,144 A | 11/2000 | Lesh |
| 6,319,280 B1 | 11/2001 | Schoon |
| 6,319,281 B1 | 11/2001 | Patel |
| 6,371,983 B1 | 4/2002 | Lane |
| 6,409,758 B2 | 6/2002 | Stobie |
| 6,425,916 B1 | 7/2002 | Garrison |
| 6,471,718 B1 | 10/2002 | Staehle |
| 6,494,909 B2 | 12/2002 | Greenhalgh |
| 6,503,272 B2 | 1/2003 | Duerig |
| 6,540,782 B1 | 4/2003 | Snyders |
| 6,589,275 B1 | 7/2003 | Ivancev |
| 6,702,826 B2 | 3/2004 | Liddicoat |
| 6,738,655 B1 | 5/2004 | Sen |
| 6,790,231 B2 | 9/2004 | Liddicoat |
| 6,790,237 B2 | 9/2004 | Stinson |
| 6,821,297 B2 | 11/2004 | Snyders |
| 6,830,585 B1 | 12/2004 | Artof |
| 6,840,957 B2 | 1/2005 | Dimatteo |
| 6,875,231 B2 | 4/2005 | Anduiza |
| 7,011,671 B2 | 3/2006 | Welch |
| 7,041,132 B2 | 5/2006 | Quijano |
| 7,044,966 B2 | 5/2006 | Svanidze |
| 7,125,420 B2 | 10/2006 | Rourke |
| 7,153,324 B2 | 12/2006 | Case |
| 7,276,077 B2 | 10/2007 | Zadno-Azizi |
| 7,364,588 B2 | 4/2008 | Mathis |
| 7,381,220 B2 | 6/2008 | Macoviak |
| 7,442,204 B2 | 10/2008 | Schwammenthal |
| 7,445,631 B2 | 11/2008 | Salahieh |
| 7,455,689 B2 | 11/2008 | Johnson |
| 7,510,572 B2 | 3/2009 | Gabbay |
| 7,524,331 B2 | 4/2009 | Birdsall |
| 7,611,534 B2 | 11/2009 | Kapadia |
| 7,704,277 B2 | 4/2010 | Zakay |
| 7,749,266 B2 | 7/2010 | Forster |
| 7,758,491 B2 | 7/2010 | Buckner |
| 7,780,723 B2 | 8/2010 | Taylor |
| 7,789,909 B2 | 9/2010 | Andersen |
| 7,935,144 B2 | 5/2011 | Robin |
| 7,959,672 B2 | 6/2011 | Salahieh |
| 7,967,853 B2 | 6/2011 | Eidenschink |
| 7,998,196 B2 | 8/2011 | Mathison |
| 8,012,201 B2 | 9/2011 | Lashinski |
| 8,016,877 B2 | 9/2011 | Seguin |
| 8,021,420 B2 | 9/2011 | Dolan |
| D648,854 S | 11/2011 | Braido |
| 8,052,592 B2 | 11/2011 | Goldfarb |
| 8,057,493 B2 | 11/2011 | Goldfarb |
| 8,070,802 B2 | 12/2011 | Lamphere |
| 8,083,793 B2 | 12/2011 | Lane |
| D653,341 S | 1/2012 | Braido |
| D653,342 S | 1/2012 | Braido |
| 8,092,524 B2 | 1/2012 | Nugent |
| 8,142,492 B2 | 3/2012 | Forster |
| 8,147,541 B2 | 4/2012 | Forster |
| D660,433 S | 5/2012 | Braido |
| D660,967 S | 5/2012 | Braido |
| 8,167,932 B2 | 5/2012 | Bourang |
| 8,236,049 B2 | 8/2012 | Rowe |
| 8,246,677 B2 | 8/2012 | Ryan |
| 8,252,051 B2 | 8/2012 | Chau |
| 8,287,538 B2 | 10/2012 | Brenzel et al. |
| 8,308,798 B2 | 11/2012 | Pintor |
| 8,348,998 B2 | 1/2013 | Pintor |
| 8,348,999 B2 | 1/2013 | Kheradvar |
| 8,366,768 B2 | 2/2013 | Zhang |
| 8,398,708 B2 | 3/2013 | Meiri |
| 8,409,275 B2 | 4/2013 | Matheny |
| 8,414,645 B2 | 4/2013 | Dwork |
| 8,439,970 B2 | 5/2013 | Jimenez |
| 8,465,541 B2 | 6/2013 | Dwork |
| 8,491,650 B2 | 7/2013 | Wiemeyer |
| 8,512,400 B2 | 8/2013 | Tran |
| 8,518,106 B2 | 8/2013 | Duffy |
| 8,535,373 B2 | 9/2013 | Stacchino |
| 8,562,673 B2 | 10/2013 | Yeung |
| 8,568,472 B2 | 10/2013 | Marchand |
| 8,579,963 B2 | 11/2013 | Tabor |
| 8,579,964 B2 | 11/2013 | Lane |
| 8,603,159 B2 | 12/2013 | Seguin |
| 8,623,075 B2 | 1/2014 | Murray, III |
| 8,636,764 B2 | 1/2014 | Miles |
| 8,641,757 B2 | 2/2014 | Pintor |
| 8,657,870 B2 | 2/2014 | Turovskiy |
| 8,663,318 B2 | 3/2014 | Ho |
| 8,679,176 B2 | 3/2014 | Matheny |
| 8,721,715 B2 | 5/2014 | Wang |
| 8,740,976 B2 | 6/2014 | Tran |
| 8,747,459 B2 | 6/2014 | Nguyen |
| 8,747,461 B2 | 6/2014 | Centola |
| 8,764,793 B2 | 7/2014 | Lee |
| 8,764,820 B2 | 7/2014 | Dehdashtian |
| 8,778,020 B2 | 7/2014 | Gregg |
| 8,790,396 B2 | 7/2014 | Bergheim |
| 8,795,354 B2 | 8/2014 | Benichou |
| 8,795,357 B2 | 8/2014 | Yohanan |
| 8,805,466 B2 | 8/2014 | Salahieh |
| 8,814,931 B2 | 8/2014 | Wang |
| 8,828,043 B2 | 9/2014 | Chambers |
| 8,828,051 B2 | 9/2014 | Javois |
| 8,845,711 B2 | 9/2014 | Miles |
| 8,845,722 B2 | 9/2014 | Gabbay |
| 8,852,271 B2 | 10/2014 | Murray, III |
| 8,852,272 B2 | 10/2014 | Gross |
| 8,870,949 B2 | 10/2014 | Rowe |
| 8,876,897 B2 | 11/2014 | Kheradvar |
| 8,906,022 B2 | 12/2014 | Krinke et al. |
| 8,926,692 B2 | 1/2015 | Dwork |
| 8,956,402 B2 | 2/2015 | Cohn |
| 8,956,405 B2 | 2/2015 | Wang |
| 8,961,518 B2 | 2/2015 | Kyle et al. |
| 8,986,372 B2 | 3/2015 | Murry, III |
| 8,986,374 B2 | 3/2015 | Cao |
| 8,986,375 B2 | 3/2015 | Garde |
| 8,998,980 B2 | 4/2015 | Shipley |
| 8,998,982 B2 | 4/2015 | Richter |
| 9,005,273 B2 | 4/2015 | Salahieh |
| 9,011,527 B2 | 4/2015 | Li |
| D730,520 S | 5/2015 | Braido |
| D730,521 S | 5/2015 | Braido |
| 9,023,101 B2 | 5/2015 | Krahbichler |
| 9,050,188 B2 | 6/2015 | Schweich, Jr. |
| 9,060,855 B2 | 6/2015 | Tuval |
| 9,060,857 B2 | 6/2015 | Nguyen |
| 9,060,858 B2 | 6/2015 | Thornton |
| 9,061,119 B2 | 6/2015 | Le |
| 9,066,800 B2 | 6/2015 | Clague |
| 9,072,603 B2 | 7/2015 | Tuval |
| 9,101,471 B2 | 8/2015 | Kleinschrodt |
| 9,119,717 B2 | 9/2015 | Wang |
| 9,132,008 B2 | 9/2015 | Dwork |
| 9,132,009 B2 | 9/2015 | Hacohen |
| 9,138,313 B2 | 9/2015 | Mcguckin, Jr. |
| 9,144,493 B2 | 9/2015 | Carr |
| 9,144,494 B2 | 9/2015 | Murray |
| 9,155,619 B2 | 10/2015 | Liu |
| 9,161,835 B2 | 10/2015 | Rankin |
| 9,173,737 B2 | 11/2015 | Hill |
| 9,226,820 B2 | 1/2016 | Braido |
| 9,232,996 B2 | 1/2016 | Sun |
| 9,248,016 B2 | 2/2016 | Oba |

(56) References Cited

U.S. PATENT DOCUMENTS

| | | |
|---|---|---|
| 9,259,315 B2 | 2/2016 | Zhou |
| 9,271,856 B2 | 3/2016 | Duffy |
| 9,277,993 B2 | 3/2016 | Gamarra |
| 9,289,289 B2 | 3/2016 | Rolando |
| 9,289,292 B2 | 3/2016 | Anderl |
| 9,295,547 B2 | 3/2016 | Costello |
| 9,295,549 B2 | 3/2016 | Braido |
| 9,301,836 B2 | 4/2016 | Buchbinder |
| 9,301,839 B2 | 4/2016 | Stante |
| 9,320,597 B2 | 4/2016 | Savage |
| 9,320,599 B2 | 4/2016 | Salahieh |
| 9,326,853 B2 | 5/2016 | Olson |
| 9,326,854 B2 | 5/2016 | Casley |
| 9,333,075 B2 | 5/2016 | Biadillah |
| 9,345,572 B2 | 5/2016 | Cerf |
| 9,351,831 B2 | 5/2016 | Braido |
| 9,358,108 B2 | 6/2016 | Bortlein |
| 9,364,325 B2 | 6/2016 | Alon |
| 9,364,637 B2 | 6/2016 | Rothstein |
| 9,370,422 B2 | 6/2016 | Wang |
| 9,387,106 B2 | 7/2016 | Stante |
| 9,402,720 B2 | 8/2016 | Richter |
| 9,414,910 B2 | 8/2016 | Lim |
| 9,414,917 B2 | 8/2016 | Young |
| 9,427,316 B2 | 8/2016 | Schweich, Jr. |
| 9,439,795 B2 | 9/2016 | Wang |
| 9,480,560 B2 | 11/2016 | Quadri |
| 9,498,370 B2 | 11/2016 | Kyle et al. |
| 9,522,062 B2 | 12/2016 | Tuval |
| 9,566,152 B2 | 2/2017 | Schweich, Jr. |
| 9,730,791 B2 | 8/2017 | Ratz |
| 9,737,400 B2 | 8/2017 | Fish |
| 9,737,401 B2 | 8/2017 | Conklin |
| 9,750,604 B2 | 9/2017 | Naor |
| 9,763,780 B2 | 9/2017 | Morriss |
| 9,795,477 B2 | 10/2017 | Tran |
| 9,801,711 B2 | 10/2017 | Gainor |
| 9,827,093 B2 | 11/2017 | Cartledge |
| 9,839,517 B2 | 12/2017 | Centola et al. |
| 9,839,765 B2 | 12/2017 | Morris |
| 9,861,477 B2 | 1/2018 | Backus |
| 9,872,765 B2 | 1/2018 | Zeng |
| 9,968,443 B2 | 5/2018 | Bruchman |
| 10,004,601 B2 | 6/2018 | Tuval |
| 10,016,274 B2 | 7/2018 | Tabor |
| 10,016,275 B2 | 7/2018 | Nyuli |
| 10,022,132 B2 | 7/2018 | Wlodarski et al. |
| 10,034,750 B2 | 7/2018 | Morriss |
| 10,039,642 B2 | 8/2018 | Hillukka |
| 10,182,907 B2 | 1/2019 | Lapeyre |
| 10,195,023 B2 | 2/2019 | Wrobel |
| 10,245,145 B2 | 4/2019 | Mantanus |
| 10,258,464 B2 | 4/2019 | Delaloye |
| 10,299,917 B2 | 5/2019 | Morriss |
| 10,321,990 B2 | 6/2019 | Braido |
| 10,327,892 B2 | 6/2019 | O'Connor |
| 10,327,893 B2 | 6/2019 | Maiorano |
| 10,350,065 B2 | 7/2019 | Quadri |
| 10,357,360 B2 | 7/2019 | Hariton |
| 10,368,982 B2 | 8/2019 | Weber |
| 10,383,725 B2 | 8/2019 | Chambers |
| 10,405,974 B2 | 9/2019 | Hayes |
| 10,433,961 B2 | 10/2019 | Mclean |
| 10,470,880 B2 | 11/2019 | Braido |
| 10,492,907 B2 | 12/2019 | Duffy |
| 10,500,041 B2 | 12/2019 | Valdez |
| 10,512,537 B2 | 12/2019 | Corbett |
| 10,512,538 B2 | 12/2019 | Alkhatib |
| 10,517,726 B2 | 12/2019 | Chau |
| 10,524,902 B2 | 1/2020 | Gründeman |
| 10,555,809 B2 | 2/2020 | Hastings |
| 10,561,495 B2 | 2/2020 | Chambers |
| 10,595,992 B2 | 3/2020 | Chambers |
| 10,610,362 B2 | 4/2020 | Quadri |
| 10,653,523 B2 | 5/2020 | Chambers |
| 10,667,909 B2 | 6/2020 | Richter |
| 10,702,379 B2 | 7/2020 | Garde |
| 10,702,380 B2 | 7/2020 | Morriss |
| 10,751,169 B2 | 8/2020 | Chambers |
| 10,751,170 B2 | 8/2020 | Richter |
| 10,751,172 B2 | 8/2020 | Para |
| 10,758,342 B2 | 9/2020 | Chau |
| 10,779,968 B2 | 9/2020 | Giasolli |
| 10,828,152 B2 | 11/2020 | Chambers |
| 10,874,513 B2 | 12/2020 | Chambers |
| 10,945,835 B2 | 3/2021 | Morriss |
| 10,973,630 B2 | 4/2021 | Torrianni |
| 10,980,636 B2 | 4/2021 | Delaloye |
| 11,000,000 B2 | 5/2021 | Diedering |
| 11,007,053 B2 | 5/2021 | Braido |
| 11,013,599 B2 | 5/2021 | Subramanian |
| 11,026,782 B2 | 6/2021 | Chambers |
| 11,033,275 B2 | 6/2021 | Franano et al. |
| 11,045,202 B2 | 6/2021 | Amplatz |
| 11,065,113 B2 | 7/2021 | Backus |
| 11,065,116 B2 | 7/2021 | Tegels |
| 11,065,138 B2 | 7/2021 | Schreck |
| 11,147,666 B2 | 10/2021 | Braido |
| 11,154,398 B2 | 10/2021 | Straubinger |
| 11,197,754 B2 | 12/2021 | Saffari |
| 11,207,176 B2 | 12/2021 | Delaloye |
| 11,278,399 B2 | 3/2022 | Liu |
| 11,278,406 B2 | 3/2022 | Straubinger |
| 11,351,028 B2 | 6/2022 | Peterson |
| 11,389,293 B2 | 7/2022 | Torrianni |
| 11,413,141 B2 | 8/2022 | Morin |
| 11,419,716 B2 | 8/2022 | Braido |
| 11,452,628 B2 | 9/2022 | Diedering |
| 2001/0005787 A1 | 6/2001 | Oz |
| 2002/0072710 A1 | 6/2002 | Stewart |
| 2002/0161377 A1 | 10/2002 | Rabkin |
| 2003/0083730 A1 | 5/2003 | Stinson |
| 2003/0199971 A1 | 10/2003 | Tower |
| 2003/0225445 A1 | 12/2003 | Derus |
| 2003/0233141 A1 | 12/2003 | Israel |
| 2004/0073286 A1 | 4/2004 | Armstrong |
| 2004/0088041 A1 | 5/2004 | Stanford |
| 2004/0138745 A1* | 7/2004 | Macoviak .......... A61F 2/2412 623/2.36 |
| 2004/0210307 A1 | 10/2004 | Khairkhahan |
| 2004/0243107 A1 | 12/2004 | Macoviak |
| 2005/0004641 A1 | 1/2005 | Pappu |
| 2005/0075727 A1 | 4/2005 | Wheatley |
| 2005/0096739 A1 | 5/2005 | Cao |
| 2005/0113861 A1 | 5/2005 | Corcoran |
| 2005/0137622 A1 | 6/2005 | Griffin |
| 2005/0197694 A1 | 9/2005 | Pai |
| 2005/0273160 A1 | 12/2005 | Lashinski |
| 2006/0142847 A1 | 6/2006 | Shaknovich |
| 2006/0184226 A1 | 8/2006 | Austin |
| 2006/0224183 A1 | 10/2006 | Freudenthal |
| 2006/0229708 A1 | 10/2006 | Powell |
| 2006/0271173 A1 | 11/2006 | Delgado, III |
| 2006/0276874 A1 | 12/2006 | Wilson |
| 2007/0173930 A1 | 7/2007 | Sogard |
| 2007/0233223 A1 | 10/2007 | Styrc |
| 2007/0238979 A1 | 10/2007 | Huynh |
| 2007/0239254 A1 | 10/2007 | Chia |
| 2007/0239271 A1 | 10/2007 | Nguyen |
| 2007/0270931 A1 | 11/2007 | Leanna |
| 2007/0275027 A1 | 11/2007 | Wen et al. |
| 2007/0293942 A1 | 12/2007 | Mirzaee |
| 2008/0039928 A1 | 2/2008 | Peacock |
| 2008/0082166 A1 | 4/2008 | Styrc |
| 2008/0262592 A1 | 10/2008 | Jordan |
| 2008/0269877 A1 | 10/2008 | Jenson |
| 2008/0275540 A1 | 11/2008 | Wen |
| 2008/0281398 A1 | 11/2008 | Koss |
| 2008/0288042 A1 | 11/2008 | Purdy |
| 2008/0288055 A1 | 11/2008 | Paul, Jr. |
| 2009/0076585 A1 | 3/2009 | Hendriksen |
| 2009/0082840 A1 | 3/2009 | Rusk |
| 2009/0099640 A1 | 4/2009 | Weng |
| 2009/0099647 A1 | 4/2009 | Glimsdale |

(56) References Cited

U.S. PATENT DOCUMENTS

| | | |
|---|---|---|
| 2009/0125096 A1 | 5/2009 | Chu |
| 2009/0143852 A1 | 6/2009 | Chambers |
| 2009/0171447 A1 | 7/2009 | Von Segesser |
| 2009/0198315 A1 | 8/2009 | Boudjemline |
| 2009/0248134 A1 | 10/2009 | Dierking |
| 2009/0270967 A1 | 10/2009 | Fleming, III |
| 2009/0276039 A1 | 11/2009 | Meretei |
| 2009/0281609 A1 | 11/2009 | Benichou |
| 2010/0021726 A1 | 1/2010 | Jo |
| 2010/0057192 A1 | 3/2010 | Celermajer |
| 2010/0069948 A1 | 3/2010 | Veznedaroglu |
| 2010/0168839 A1 | 7/2010 | Braido |
| 2010/0174355 A1 | 7/2010 | Boyle |
| 2010/0217260 A1 | 8/2010 | Aramayo |
| 2010/0217261 A1 | 8/2010 | Watson |
| 2010/0217262 A1 | 8/2010 | Stevenson |
| 2010/0217263 A1 | 8/2010 | Tukulj-Popovic |
| 2010/0217264 A1 | 8/2010 | Odom |
| 2010/0217265 A1 | 8/2010 | Chen |
| 2010/0217266 A1 | 8/2010 | Helevirta |
| 2010/0217267 A1 | 8/2010 | Bergin |
| 2010/0217268 A1 | 8/2010 | Bloebaum |
| 2010/0217269 A1 | 8/2010 | Landes |
| 2010/0256749 A1 | 10/2010 | Tran |
| 2010/0262157 A1 | 10/2010 | Silver |
| 2011/0022151 A1 | 1/2011 | Shin |
| 2011/0046712 A1 | 2/2011 | Melsheimer |
| 2011/0082539 A1 | 4/2011 | Suri |
| 2011/0082540 A1 | 4/2011 | Forster |
| 2011/0208293 A1 | 8/2011 | Tabor |
| 2011/0218585 A1 | 9/2011 | Krinke et al. |
| 2011/0251676 A1 | 10/2011 | Sweeney |
| 2011/0301702 A1 | 12/2011 | Rust |
| 2011/0319988 A1 | 12/2011 | Schankereli |
| 2011/0319991 A1 | 12/2011 | Hariton |
| 2012/0016468 A1 | 1/2012 | Robin |
| 2012/0035719 A1 | 2/2012 | Forster |
| 2012/0078356 A1 | 3/2012 | Fish |
| 2012/0083875 A1 | 4/2012 | Johnson |
| 2012/0095551 A1 | 4/2012 | Navia |
| 2012/0101567 A1 | 4/2012 | Jansen |
| 2012/0101571 A1 | 4/2012 | Thambar |
| 2012/0109079 A1 | 5/2012 | Asleson |
| 2012/0197193 A1 | 8/2012 | Krolik et al. |
| 2012/0197390 A1 | 8/2012 | Alkhatib |
| 2012/0209375 A1 | 8/2012 | Madrid |
| 2012/0226130 A1 | 9/2012 | De Graff |
| 2012/0303048 A1 | 11/2012 | Manasse |
| 2012/0323313 A1 | 12/2012 | Seguin |
| 2013/0023852 A1 | 1/2013 | Drasler |
| 2013/0060329 A1 | 3/2013 | Agnew |
| 2013/0066419 A1 | 3/2013 | Gregg |
| 2013/0079872 A1 | 3/2013 | Gallagher |
| 2013/0096671 A1 | 4/2013 | Iobbi |
| 2013/0123911 A1 | 5/2013 | Chalekian |
| 2013/0138138 A1 | 5/2013 | Clark |
| 2013/0150956 A1 | 6/2013 | Yohanan |
| 2013/0184811 A1 | 7/2013 | Rowe |
| 2013/0190861 A1 | 7/2013 | Chau |
| 2013/0204311 A1 | 8/2013 | Kunis |
| 2013/0204360 A1 | 8/2013 | Gainor |
| 2013/0231736 A1 | 9/2013 | Essinger |
| 2013/0238089 A1 | 9/2013 | Lichtenstein |
| 2013/0297010 A1 | 11/2013 | Bishop |
| 2013/0297012 A1 | 11/2013 | Willard |
| 2013/0304197 A1 | 11/2013 | Buchbinder |
| 2013/0310917 A1 | 11/2013 | Richter |
| 2013/0310923 A1 | 11/2013 | Kheradvar |
| 2013/0317598 A1 | 11/2013 | Rowe |
| 2013/0331933 A1 | 12/2013 | Alkhatib |
| 2014/0005768 A1 | 1/2014 | Thomas |
| 2014/0005773 A1 | 1/2014 | Wheatley |
| 2014/0005778 A1 | 1/2014 | Buchbinder |
| 2014/0012371 A1 | 1/2014 | Li |
| 2014/0018841 A1 | 1/2014 | Peiffer |
| 2014/0018906 A1 | 1/2014 | Rafiee |
| 2014/0031928 A1 | 1/2014 | Murphy |
| 2014/0031951 A1 | 1/2014 | Costello |
| 2014/0039613 A1 | 2/2014 | Navia |
| 2014/0046433 A1 | 2/2014 | Kovalsky |
| 2014/0046436 A1 | 2/2014 | Kheradvar |
| 2014/0052238 A1 | 2/2014 | Wang |
| 2014/0052241 A1 | 2/2014 | Harks |
| 2014/0057730 A1 | 2/2014 | Steinhauser |
| 2014/0057731 A1 | 2/2014 | Stephens |
| 2014/0057732 A1 | 2/2014 | Gilbert |
| 2014/0057733 A1 | 2/2014 | Yamamoto |
| 2014/0057734 A1 | 2/2014 | Lu |
| 2014/0057735 A1 | 2/2014 | Yu |
| 2014/0057736 A1 | 2/2014 | Burnett |
| 2014/0057737 A1 | 2/2014 | Solheim |
| 2014/0057738 A1 | 2/2014 | Albertsen |
| 2014/0057739 A1 | 2/2014 | Stites |
| 2014/0067050 A1 | 3/2014 | Costello |
| 2014/0074151 A1 | 3/2014 | Tischler |
| 2014/0081308 A1 | 3/2014 | Wondka |
| 2014/0081375 A1 | 3/2014 | Bardill et al. |
| 2014/0088696 A1 | 3/2014 | Figulla |
| 2014/0114340 A1 | 4/2014 | Zhou |
| 2014/0128963 A1 | 5/2014 | Quill |
| 2014/0134322 A1 | 5/2014 | Larsen |
| 2014/0135817 A1 | 5/2014 | Tischler |
| 2014/0135907 A1 | 5/2014 | Gallagher |
| 2014/0142612 A1 | 5/2014 | Li |
| 2014/0142680 A1 | 5/2014 | Laske |
| 2014/0142688 A1 | 5/2014 | Duffy |
| 2014/0163668 A1 | 6/2014 | Rafiee |
| 2014/0172076 A1 | 6/2014 | Jonsson |
| 2014/0172083 A1 | 6/2014 | Bruchman |
| 2014/0180397 A1 | 6/2014 | Gerberding |
| 2014/0180401 A1 | 6/2014 | Quill |
| 2014/0188157 A1 | 7/2014 | Clark |
| 2014/0194979 A1 | 7/2014 | Seguin |
| 2014/0222140 A1 | 8/2014 | Schreck |
| 2014/0228944 A1 | 8/2014 | Paniagua |
| 2014/0236288 A1 | 8/2014 | Lambrecht |
| 2014/0243954 A1 | 8/2014 | Shannon |
| 2014/0243967 A1 | 8/2014 | Salahieh |
| 2014/0243969 A1 | 8/2014 | Venkatasubramanian |
| 2014/0249564 A1 | 9/2014 | Daly |
| 2014/0249621 A1 | 9/2014 | Eidenschink |
| 2014/0257467 A1 | 9/2014 | Lane |
| 2014/0276395 A1 | 9/2014 | Wilson |
| 2014/0277074 A1 | 9/2014 | Kaplan |
| 2014/0277119 A1 | 9/2014 | Akpinar |
| 2014/0277388 A1 | 9/2014 | Skemp |
| 2014/0277389 A1 | 9/2014 | Braido |
| 2014/0277408 A1 | 9/2014 | Folan |
| 2014/0277411 A1 | 9/2014 | Börtlein |
| 2014/0277417 A1 | 9/2014 | Schraut |
| 2014/0277422 A1 | 9/2014 | Ratz |
| 2014/0277424 A1 | 9/2014 | Oslund |
| 2014/0277425 A1 | 9/2014 | Dakin |
| 2014/0277426 A1 | 9/2014 | Dakin |
| 2014/0288634 A1 | 9/2014 | Shalev |
| 2014/0288639 A1 | 9/2014 | Gainor |
| 2014/0296909 A1 | 10/2014 | Heipl |
| 2014/0296969 A1 | 10/2014 | Tegels |
| 2014/0296970 A1 | 10/2014 | Ekvall |
| 2014/0296975 A1 | 10/2014 | Tegels |
| 2014/0309727 A1 | 10/2014 | Lamelas et al. |
| 2014/0330366 A1 | 11/2014 | Dehdashtian |
| 2014/0330368 A1 | 11/2014 | Gloss |
| 2014/0330369 A1 | 11/2014 | Matheny |
| 2014/0330370 A1 | 11/2014 | Matheny |
| 2014/0331475 A1 | 11/2014 | Duffy |
| 2014/0343665 A1 | 11/2014 | Straubinger |
| 2014/0343669 A1 | 11/2014 | Lane |
| 2014/0343670 A1 | 11/2014 | Bakis |
| 2014/0371844 A1 | 12/2014 | Dale |
| 2014/0379020 A1 | 12/2014 | Campbell |
| 2015/0005857 A1 | 1/2015 | Kern |
| 2015/0018933 A1 | 1/2015 | Yang |
| 2015/0025621 A1 | 1/2015 | Costello |

(56) References Cited

U.S. PATENT DOCUMENTS

| | | |
|---|---|---|
| 2015/0025625 A1 | 1/2015 | Rylski |
| 2015/0039081 A1 | 2/2015 | Costello |
| 2015/0039083 A1 | 2/2015 | Rafiee |
| 2015/0066138 A1 | 3/2015 | Alexander |
| 2015/0066141 A1 | 3/2015 | Braido |
| 2015/0073548 A1 | 3/2015 | Matheny |
| 2015/0088251 A1 | 3/2015 | May-Newman |
| 2015/0094802 A1 | 4/2015 | Buchbinder |
| 2015/0094804 A1 | 4/2015 | Bonhoeffer |
| 2015/0112428 A1 | 4/2015 | Daly |
| 2015/0112430 A1 | 4/2015 | Creaven |
| 2015/0119974 A1 | 4/2015 | Rothstein |
| 2015/0119978 A1 | 4/2015 | Tegels |
| 2015/0119980 A1 | 4/2015 | Beith |
| 2015/0119982 A1 | 4/2015 | Quill |
| 2015/0127032 A1 | 5/2015 | Lentz |
| 2015/0127093 A1 | 5/2015 | Hosmer |
| 2015/0127097 A1 | 5/2015 | Neumann |
| 2015/0127100 A1 | 5/2015 | Braido |
| 2015/0134054 A1 | 5/2015 | Morrissey |
| 2015/0142103 A1 | 5/2015 | Vidlund |
| 2015/0142104 A1 | 5/2015 | Braido |
| 2015/0148731 A1 | 5/2015 | Mcnamara |
| 2015/0150678 A1 | 6/2015 | Brecker |
| 2015/0157455 A1 | 6/2015 | Hoang |
| 2015/0157458 A1 | 6/2015 | Thambar |
| 2015/0173770 A1 | 6/2015 | Warner |
| 2015/0173897 A1 | 6/2015 | Raanani |
| 2015/0173898 A1 | 6/2015 | Drasler |
| 2015/0173899 A1 | 6/2015 | Braido |
| 2015/0196300 A1 | 7/2015 | Tischler |
| 2015/0196390 A1 | 7/2015 | Ma |
| 2015/0196393 A1 | 7/2015 | Vidlund |
| 2015/0209140 A1 | 7/2015 | Bell |
| 2015/0209143 A1 | 7/2015 | Duffy |
| 2015/0223729 A1 | 8/2015 | Balachandran |
| 2015/0223820 A1 | 8/2015 | Olson |
| 2015/0223934 A1 | 8/2015 | Vidlund |
| 2015/0230921 A1 | 8/2015 | Chau |
| 2015/0238312 A1 | 8/2015 | Lashinski |
| 2015/0238313 A1 | 8/2015 | Spence |
| 2015/0257879 A1 | 9/2015 | Bortlein |
| 2015/0257880 A1 | 9/2015 | Bortlein |
| 2015/0257881 A1 | 9/2015 | Bortlein |
| 2015/0257882 A1 | 9/2015 | Bortlein |
| 2015/0265402 A1 | 9/2015 | Centola |
| 2015/0265404 A1 | 9/2015 | Rankin |
| 2015/0272730 A1 | 10/2015 | Melnick |
| 2015/0272731 A1 | 10/2015 | Racchini |
| 2015/0272738 A1 | 10/2015 | Sievers |
| 2015/0282931 A1 | 10/2015 | Brunnett |
| 2015/0282958 A1 | 10/2015 | Centola |
| 2015/0289972 A1 | 10/2015 | Yang |
| 2015/0289974 A1 | 10/2015 | Matheny |
| 2015/0289977 A1 | 10/2015 | Kovalsky |
| 2015/0290007 A1 | 10/2015 | Aggerholm |
| 2015/0297346 A1 | 10/2015 | Duffy |
| 2015/0297381 A1 | 10/2015 | Essinger |
| 2015/0305860 A1 | 10/2015 | Wang |
| 2015/0305861 A1 | 10/2015 | Annest |
| 2015/0313710 A1 | 11/2015 | Eberhardt |
| 2015/0313712 A1 | 11/2015 | Carpentier |
| 2015/0320552 A1 | 11/2015 | Letac |
| 2015/0320556 A1 | 11/2015 | Levi |
| 2015/0327995 A1 | 11/2015 | Morin |
| 2015/0327996 A1 | 11/2015 | Fahim |
| 2015/0327999 A1 | 11/2015 | Board |
| 2015/0328000 A1 | 11/2015 | Ratz et al. |
| 2015/0335422 A1 | 11/2015 | Straka |
| 2015/0342718 A1 | 12/2015 | Weber |
| 2015/0342734 A1 | 12/2015 | Braido |
| 2015/0351735 A1 | 12/2015 | Keranen |
| 2015/0351904 A1 | 12/2015 | Cooper |
| 2015/0351905 A1 | 12/2015 | Benson |
| 2015/0359628 A1 | 12/2015 | Keranen |
| 2015/0359629 A1 | 12/2015 | Ganesan |
| 2015/0366665 A1 | 12/2015 | Lombardi |
| 2015/0366667 A1 | 12/2015 | Bailey |
| 2015/0366690 A1 | 12/2015 | Lumauig |
| 2015/0374490 A1 | 12/2015 | Alkhatib |
| 2015/0374906 A1 | 12/2015 | Forsell |
| 2016/0000559 A1 | 1/2016 | Chen |
| 2016/0000562 A1 | 1/2016 | Siegel |
| 2016/0008128 A1 | 1/2016 | Squara |
| 2016/0008131 A1 | 1/2016 | Christianson |
| 2016/0015512 A1 | 1/2016 | Zhang |
| 2016/0015515 A1 | 1/2016 | Lashinski |
| 2016/0022417 A1 | 1/2016 | Karapetian |
| 2016/0022418 A1 | 1/2016 | Salahieh |
| 2016/0030165 A1 | 2/2016 | Mitra |
| 2016/0030168 A1 | 2/2016 | Spenser |
| 2016/0030169 A1 | 2/2016 | Shahriari |
| 2016/0030170 A1 | 2/2016 | Alkhatib |
| 2016/0030171 A1 | 2/2016 | Quijano |
| 2016/0030173 A1 | 2/2016 | Cai |
| 2016/0030175 A1 | 2/2016 | Madjarov |
| 2016/0038283 A1 | 2/2016 | Divekar |
| 2016/0045306 A1 | 2/2016 | Agrawal |
| 2016/0045308 A1 | 2/2016 | Macoviak |
| 2016/0045309 A1 | 2/2016 | Valdez |
| 2016/0045310 A1 | 2/2016 | Alkhatib |
| 2016/0045311 A1 | 2/2016 | Mccann |
| 2016/0051358 A1 | 2/2016 | Sutton |
| 2016/0051362 A1 | 2/2016 | Cooper |
| 2016/0051364 A1 | 2/2016 | Cunningham |
| 2016/0066922 A1 | 3/2016 | Bridgeman |
| 2016/0067038 A1 | 3/2016 | Park |
| 2016/0067041 A1 | 3/2016 | Alkhatib |
| 2016/0074161 A1 | 3/2016 | Bennett |
| 2016/0074164 A1 | 3/2016 | Naor |
| 2016/0074165 A1 | 3/2016 | Spence |
| 2016/0081799 A1 | 3/2016 | Leo |
| 2016/0089234 A1 | 3/2016 | Gifford, III |
| 2016/0089235 A1 | 3/2016 | Yellin |
| 2016/0089236 A1 | 3/2016 | Kovalsky |
| 2016/0095700 A1 | 4/2016 | Righini |
| 2016/0095701 A1 | 4/2016 | Dale |
| 2016/0095702 A1 | 4/2016 | Gainor |
| 2016/0095703 A1 | 4/2016 | Thomas |
| 2016/0095704 A1 | 4/2016 | Whitman |
| 2016/0100844 A1 | 4/2016 | Li |
| 2016/0100939 A1 | 4/2016 | Armstrong |
| 2016/0100941 A1 | 4/2016 | Czyscon |
| 2016/0100942 A1 | 4/2016 | Morrissey |
| 2016/0106539 A1 | 4/2016 | Buchbinder |
| 2016/0113764 A1 | 4/2016 | Sheahan |
| 2016/0113766 A1 | 4/2016 | Ganesan |
| 2016/0113767 A1 | 4/2016 | Miller |
| 2016/0113768 A1 | 4/2016 | Ganesan |
| 2016/0120642 A1 | 5/2016 | Shaolian |
| 2016/0120643 A1 | 5/2016 | Kupumbati |
| 2016/0120646 A1 | 5/2016 | Dwork |
| 2016/0135951 A1 | 5/2016 | Salahieh |
| 2016/0136412 A1 | 5/2016 | Mckinnon |
| 2016/0143730 A1 | 5/2016 | Kheradvar |
| 2016/0143731 A1 | 5/2016 | Backus |
| 2016/0143734 A1 | 5/2016 | Shaolian |
| 2016/0151155 A1 | 6/2016 | Lutter |
| 2016/0157998 A1 | 6/2016 | Bruchman |
| 2016/0157999 A1 | 6/2016 | Lane |
| 2016/0158001 A1 | 6/2016 | Wallace |
| 2016/0158004 A1 | 6/2016 | Kumar |
| 2016/0158007 A1 | 6/2016 | Centola |
| 2016/0158011 A1 | 6/2016 | De Canniere |
| 2016/0158013 A1 | 6/2016 | Carpentier |
| 2016/0166381 A1 | 6/2016 | Sugimoto |
| 2016/0166382 A1 | 6/2016 | Nguyen |
| 2016/0166384 A1 | 6/2016 | Olson |
| 2016/0175096 A1 | 6/2016 | Dienno |
| 2016/0193044 A1 | 7/2016 | Achiluzzi |
| 2016/0193045 A1 | 7/2016 | Pollak |
| 2016/0193047 A1 | 7/2016 | Delaloye |
| 2016/0199177 A1 | 7/2016 | Spence |
| 2016/0199178 A1 | 7/2016 | Venkatasubramanian |

(56) References Cited

U.S. PATENT DOCUMENTS

| | | |
|---|---|---|
| 2016/0199180 A1 | 7/2016 | Zeng |
| 2016/0199182 A1 | 7/2016 | Gorman, III |
| 2016/0213470 A1 | 7/2016 | Ahlberg |
| 2016/0220363 A1 | 8/2016 | Peter |
| 2016/0235525 A1 | 8/2016 | Rothstein |
| 2016/0235530 A1 | 8/2016 | Thomas |
| 2016/0235531 A1 | 8/2016 | Ciobanu |
| 2016/0242905 A1 | 8/2016 | Chambers |
| 2016/0250022 A1 | 9/2016 | Braido |
| 2016/0256270 A1 | 9/2016 | Folan |
| 2016/0262884 A1 | 9/2016 | Lombardi |
| 2016/0270910 A1 | 9/2016 | Birmingham |
| 2016/0270911 A1 | 9/2016 | Ganesan |
| 2016/0278922 A1 | 9/2016 | Braido |
| 2016/0296323 A1 | 10/2016 | Wulfman |
| 2016/0296333 A1 | 10/2016 | Balachandran |
| 2016/0302920 A1 | 10/2016 | Al-Jilaihawi |
| 2016/0302921 A1 | 10/2016 | Gosal |
| 2016/0302922 A1 | 10/2016 | Keidar |
| 2016/0310268 A1 | 10/2016 | Oba |
| 2016/0324640 A1 | 11/2016 | Gifford, III |
| 2016/0324641 A1 | 11/2016 | Solem |
| 2016/0331529 A1 | 11/2016 | Marchand |
| 2016/0354203 A1 | 12/2016 | Tuval et al. |
| 2016/0361161 A1 | 12/2016 | Braido |
| 2016/0374790 A1 | 12/2016 | Jacinto |
| 2016/0374801 A1 | 12/2016 | Jimenez |
| 2016/0374802 A1 | 12/2016 | Levi |
| 2016/0374803 A1 | 12/2016 | Figulla |
| 2016/0374842 A1 | 12/2016 | Havel |
| 2017/0079785 A1 | 3/2017 | Li |
| 2017/0079787 A1 | 3/2017 | Benson |
| 2017/0079790 A1 | 3/2017 | Vidlund |
| 2017/0086973 A1 | 3/2017 | Zeng |
| 2017/0100241 A1 | 4/2017 | Modine |
| 2017/0105839 A1 | 4/2017 | Subramanian |
| 2017/0165066 A1 | 6/2017 | Rothstein |
| 2017/0172737 A1* | 6/2017 | Kuetting ............. A61F 2/2418 |
| 2017/0252191 A1 | 9/2017 | Pacetti |
| 2017/0348098 A1 | 12/2017 | Rowe |
| 2017/0360570 A1 | 12/2017 | Berndt et al. |
| 2018/0055629 A1 | 3/2018 | Oba et al. |
| 2018/0092744 A1 | 4/2018 | Von Oepen |
| 2018/0116848 A1 | 5/2018 | Mchugo |
| 2018/0185184 A1 | 7/2018 | Christakis |
| 2018/0193153 A1 | 7/2018 | Brenzel et al. |
| 2018/0206983 A1 | 7/2018 | Noe |
| 2018/0256329 A1 | 9/2018 | Chambers |
| 2018/0296335 A1 | 10/2018 | Miyashiro |
| 2018/0311039 A1 | 11/2018 | Cohen |
| 2018/0325664 A1 | 11/2018 | Gonda |
| 2018/0333102 A1 | 11/2018 | Peterson et al. |
| 2018/0360602 A1 | 12/2018 | Kumar |
| 2018/0369006 A1 | 12/2018 | Zhang |
| 2019/0053898 A1 | 2/2019 | Maimon et al. |
| 2019/0099265 A1 | 4/2019 | Braido |
| 2019/0105088 A1 | 4/2019 | Peterson et al. |
| 2019/0201192 A1 | 7/2019 | Kruse |
| 2019/0224028 A1 | 7/2019 | Finn |
| 2019/0247189 A1 | 8/2019 | Dale |
| 2019/0321530 A1 | 10/2019 | Cambronne |
| 2019/0365534 A1 | 12/2019 | Kramer |
| 2019/0365538 A1 | 12/2019 | Chambers |
| 2020/0000592 A1 | 1/2020 | Lee |
| 2020/0030088 A1 | 1/2020 | Vidlund |
| 2020/0030507 A1 | 1/2020 | Higgins |
| 2020/0069423 A1 | 3/2020 | Peterson |
| 2020/0069449 A1 | 3/2020 | Diedering |
| 2020/0100897 A1 | 4/2020 | Mclean |
| 2020/0113682 A1 | 4/2020 | Chang |
| 2020/0113719 A1 | 4/2020 | Desrosiers et al. |
| 2020/0129294 A1 | 4/2020 | Hariton |
| 2020/0155306 A1 | 5/2020 | Bonyuet |
| 2020/0163765 A1 | 5/2020 | Christianson |
| 2020/0179111 A1 | 6/2020 | Vidlund |
| 2020/0179115 A1 | 6/2020 | Chambers |
| 2020/0188101 A1 | 6/2020 | Chambers |
| 2020/0222179 A1 | 7/2020 | Chambers |
| 2020/0253733 A1 | 8/2020 | Subramanian |
| 2020/0261219 A1 | 8/2020 | Kumar |
| 2020/0276013 A1 | 9/2020 | Chambers |
| 2020/0315678 A1 | 10/2020 | Mazzio et al. |
| 2020/0337765 A1 | 10/2020 | Smith |
| 2020/0375733 A1 | 12/2020 | Diedering |
| 2021/0236274 A1 | 8/2021 | Benson |
| 2021/0236276 A1 | 8/2021 | Diedering |
| 2021/0275297 A1 | 9/2021 | Berndt |
| 2021/0275301 A1 | 9/2021 | Kumar |
| 2021/0290383 A1 | 9/2021 | Chambers |
| 2022/0338979 A1 | 10/2022 | Benichou |
| 2023/0218397 A1 | 7/2023 | Chambers et al. |
| 2023/0372089 A1 | 11/2023 | Kumar |

FOREIGN PATENT DOCUMENTS

| | | |
|---|---|---|
| AU | 2013201970 B2 | 3/2016 |
| CA | 2926531 A1 | 4/2015 |
| CA | 2982609 A1 | 11/2016 |
| CN | 2820130 Y | 9/2006 |
| CN | 100413471 C | 8/2008 |
| CN | 100444811 C | 12/2008 |
| CN | 101953723 A | 1/2011 |
| CN | 101953724 A | 1/2011 |
| CN | 101953725 A | 1/2011 |
| CN | 101953728 A | 1/2011 |
| CN | 101953729 A | 1/2011 |
| CN | 101961269 A | 2/2011 |
| CN | 101961273 A | 2/2011 |
| CN | 102036622 | 4/2011 |
| CN | 201870772 U | 6/2011 |
| CN | 102805676 A | 12/2012 |
| CN | 103190968 A | 7/2013 |
| CN | 203290964 U | 11/2013 |
| CN | 103431931 A | 12/2013 |
| CN | 203379235 U | 1/2014 |
| CN | 103598939 A | 2/2014 |
| CN | 103610520 A | 3/2014 |
| CN | 203619728 U | 6/2014 |
| CN | 203677318 U | 7/2014 |
| CN | 104287804 A | 1/2015 |
| CN | 104352261 A | 2/2015 |
| CN | 204133530 U | 2/2015 |
| CN | 204181679 U | 3/2015 |
| CN | 204246182 U | 4/2015 |
| CN | 204318826 U | 5/2015 |
| CN | 104688292 A | 6/2015 |
| CN | 102985033 B | 8/2015 |
| CN | 204581598 U | 8/2015 |
| CN | 204581599 U | 8/2015 |
| CN | 204683686 U | 10/2015 |
| CN | 105596052 A | 5/2016 |
| CN | 105615936 A | 6/2016 |
| CN | 205286438 U | 6/2016 |
| CN | 105873545 A | 8/2016 |
| CN | 106102658 A | 11/2016 |
| CN | 106456323 A | 2/2017 |
| CN | 108348270 | 7/2018 |
| CN | 105792780 B | 11/2018 |
| CN | 109561961 A | 4/2019 |
| CN | 107157622 B | 12/2019 |
| CN | 107252363 B | 4/2020 |
| CN | 106913909 B | 9/2020 |
| CN | 107007887 B | 10/2020 |
| DE | 102010021345 A1 | 11/2011 |
| DE | 102015004246 A1 | 10/2016 |
| DE | 102015005933 A1 | 11/2016 |
| DE | 102015005934 A1 | 11/2016 |
| EP | 1365702 A2 | 12/2003 |
| EP | 0856300 B1 | 12/2004 |
| EP | 1039851 B1 | 7/2005 |
| EP | 1401359 B1 | 8/2009 |
| EP | 2258312 B9 | 9/2012 |
| EP | 1919397 B1 | 1/2013 |
| EP | 2382336 B1 | 3/2013 |

(56) References Cited

FOREIGN PATENT DOCUMENTS

| | | |
|---|---|---|
| EP | 2596754 A1 | 5/2013 |
| EP | 2640314 A2 | 9/2013 |
| EP | 2081519 B1 | 4/2014 |
| EP | 2732796 A1 | 5/2014 |
| EP | 2651335 B1 | 10/2014 |
| EP | 2856946 A1 | 4/2015 |
| EP | 2470120 B1 | 12/2015 |
| EP | 2967858 A2 | 1/2016 |
| EP | 2 982 336 | 2/2016 |
| EP | 2982336 A1 | 2/2016 |
| EP | 3000437 | 3/2016 |
| EP | 2237746 B1 | 5/2016 |
| EP | 2991587 A4 | 5/2016 |
| EP | 3337428 A1 | 6/2018 |
| EP | 2967845 B1 | 8/2018 |
| EP | 2120794 B1 | 3/2019 |
| EP | 3389564 B1 | 2/2020 |
| EP | 2437688 B1 | 5/2020 |
| EP | 2982337 B1 | 8/2020 |
| EP | 3043745 B1 | 10/2020 |
| EP | 3490501 B1 | 10/2020 |
| EP | 2950752 B1 | 7/2022 |
| EP | 2810620 B1 | 9/2022 |
| JP | 4174184 B2 | 10/2008 |
| JP | 2015516217 A | 6/2015 |
| JP | 2016067931 A | 5/2016 |
| JP | 5995110 B2 | 9/2016 |
| JP | 2016531722 A | 10/2016 |
| JP | 2016504136 A5 | 3/2017 |
| JP | 2017506988 A | 3/2017 |
| JP | 2016520391 A5 | 4/2017 |
| JP | 2016506794 A5 | 7/2018 |
| JP | 2018535074 A5 | 12/2019 |
| WO | WO1995016476 A1 | 6/1995 |
| WO | WO2008051554 A3 | 5/2008 |
| WO | WO2009045331 A1 | 4/2009 |
| WO | WO2009127973 A2 | 10/2009 |
| WO | WO2014210299 A1 | 12/2014 |
| WO | WO2015004173 A1 | 1/2015 |
| WO | WO2015142834 A1 | 9/2015 |
| WO | WO2015152980 A1 | 10/2015 |
| WO | WO2015175524 A1 | 11/2015 |
| WO | WO2015176160 A1 | 11/2015 |
| WO | WO2015189307 A1 | 12/2015 |
| WO | WO2016016899 A1 | 2/2016 |
| WO | WO2016033170 A1 | 3/2016 |
| WO | WO2016077783 A1 | 5/2016 |
| WO | WO2016083551 A1 | 6/2016 |
| WO | WO2016100806 A1 | 6/2016 |
| WO | WO2016130524 A1 | 8/2016 |
| WO | WO2016130820 A1 | 8/2016 |
| WO | WO2016133950 A1 | 8/2016 |
| WO | WO2016112085 A3 | 9/2016 |
| WO | WO2016145250 A1 | 9/2016 |
| WO | WO2016150806 A1 | 9/2016 |
| WO | WO2016168609 A1 | 10/2016 |
| WO | WO2016191324 A1 | 12/2016 |
| WO | WO2016186909 A8 | 1/2017 |
| WO | WO2017061956 A1 | 4/2017 |
| WO | WO2017070322 A1 | 4/2017 |
| WO | WO2017151566 A1 | 9/2017 |
| WO | WO2017194504 A1 | 11/2017 |
| WO | WO2019006387 | 1/2019 |
| WO | WO2019028264 A1 | 2/2019 |

OTHER PUBLICATIONS

International Search Report and Written Opinion issued in related PCT application, mailed May 29, 2018.
Extended Search Report issued by the European Patent Office in Application No. 18764951.2, dated Oct. 26, 2020.
Australian Office Action in Application No. 2018231187, Oct. 11, 2019.
Canadian Office Action in Application No. 3,054,814, Oct. 22, 2020.
Canadian Office Action in Application No. 3,054,814, May 28, 2021.
Chinese Office Action and translation in Application No. 201880024605. 0, Apr. 6, 2021.
European Office Action in Application No. 18764951.2, Mar. 11, 2020.
Indian Office Action in Application No. 201937034716, Jan. 20, 2022.
Japanese Office Action and translation in Application No. 2019-548635 Jan. 18, 2022.
Japanese Office Action and translation in Application No. 2019-548635 Sep. 13, 2022.
International Search Report and Written Opinion in Application No. PCT/US18/21244, May 29, 2018.
Reed Miller, Start-Up Spotlight: 4C Addresses Mitral Regurgitation with Unique 'Dome' Device, https://medtech.citeline.com/MT105076/StartUp-Spotlight-4C-Addresses-Mitral-Regurgitation-With-Unique-Dome-Device Published by Citeline on Jun. 29, 2017.
A Novel Transcatheter Mitral Valve Replacement System, Dr. Phillippe Genereux, MD, Jun. 14, 2017.

* cited by examiner

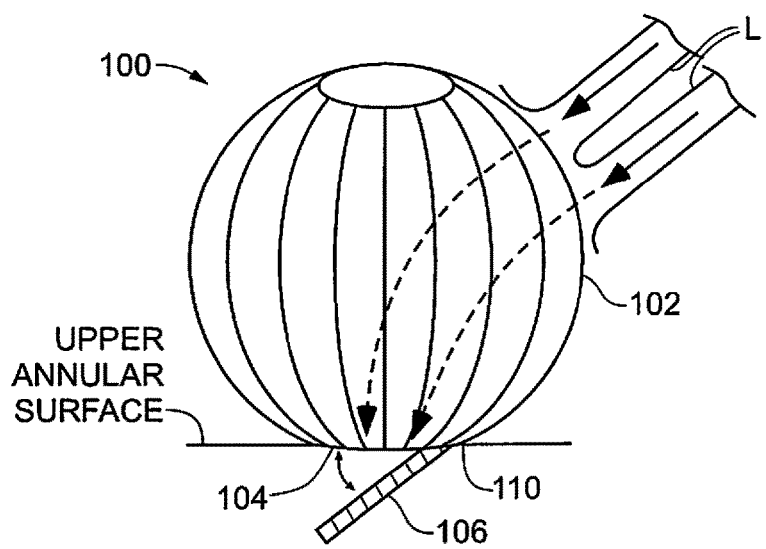
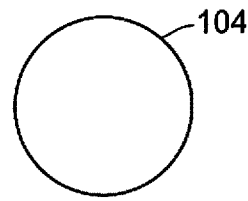
FIG. 1A
FIG. 1B
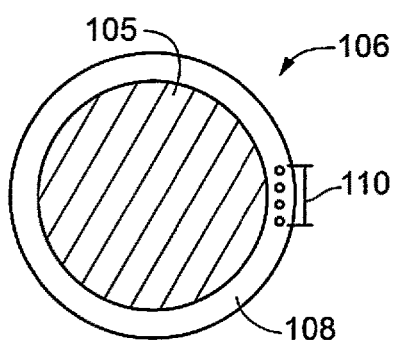
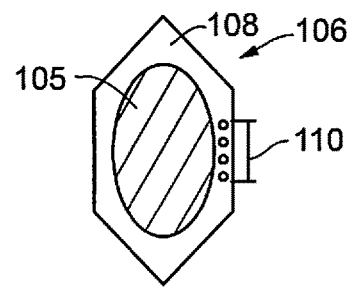
FIG. 2A
FIG. 2B
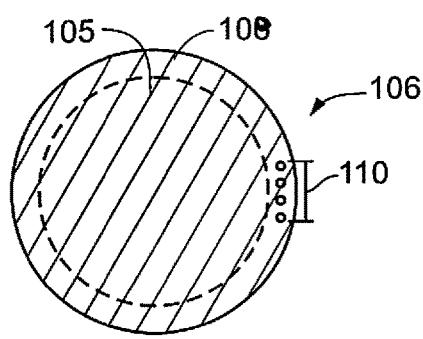
FIG. 2C

SYSTEMS, METHODS AND DEVICES FOR PROSTHETIC HEART VALVE WITH SINGLE VALVE LEAFLET

CROSS-REFERENCE TO RELATED APPLICATIONS

This application claims the benefit of U.S. Provisional Application Ser. No. 62/468,112, filed Mar. 7, 2017, and titled SYSTEMS, METHODS AND DEVICES FOR PROSTHETIC HEART VALVE WITH SINGLE VALVE LEAFLET, the entire contents of which are incorporated herein by reference.

STATEMENT REGARDING FEDERALLY SPONSORED RESEARCH OR DEVELOPMENT

Not Applicable

INCORPORATION BY REFERENCE

All references, including but not limited to publications, patent applications and patents mentioned in this specification are hereby incorporated by reference to the same extent and with the same effect as if each reference was specifically and individually indicated to be incorporated by reference.

BACKGROUND OF THE INVENTION

Field of the Invention

The invention relates to supplementing and/or replacing native heart valve leaflet function.

Description of the Related Art

The human heart comprises four chambers and four heart valves that assist in the forward (antegrade) flow of blood through the heart. The chambers include the left atrium, left ventricle, right atrium and left ventricle. The four heart valves include the mitral valve, the tricuspid valve, the aortic valve and the pulmonary valve.

The mitral valve is located between the left atrium and left ventricle and helps control the flow of blood from the left atrium to the left ventricle by acting as a one-way valve to prevent backflow into the left atrium. Similarly, the tricuspid valve is located between the right atrium and the right ventricle, while the aortic valve and the pulmonary valve are semilunar valves located in arteries flowing blood away from the heart. The valves are all one-way valves, with leaflets that open to allow forward (antegrade) blood flow. The normally functioning valve leaflets close under the pressure exerted by reverse blood to prevent backflow (retrograde) of the blood into the chamber it just flowed out of.

Native heart valves may be, or become, dysfunctional for a variety of reasons and/or conditions including but not limited to disease, trauma, congenital malformations, and aging. These types of conditions may cause the valve structure to either fail to properly open (stenotic failure) and/or fail to close properly (regurgitant).

Mitral valve regurgitation is a specific problem resulting from a dysfunctional mitral valve. Mitral regurgitation results from the mitral valve allowing at least some retrograde blood flow back into the left atrium from the left ventricle. This backflow of blood places a burden on the left ventricle with a volume load that may lead to a series of left ventricular compensatory adaptations and adjustments, including remodeling of the ventricular chamber size and shape, that vary considerably during the prolonged clinical course of mitral regurgitation.

A similar problem may occur when the tricuspid valve weakens or begins to fail. The tricuspid valve separates the right atrium and right ventricle. Tricuspid regurgitation, also known as tricuspid insufficiency, occurs when the tricuspid valve doesn't properly close, causing blood to flow back up into the right atrium when the right ventricle contracts. Various embodiments of the present invention discussed herein may apply to mitral valve and/or tricuspid valve regurgitation.

Native heart valves generally, e.g., mitral valves, therefore, may require functional repair and/or assistance, including a partial or complete replacement. Such intervention may take several forms including open heart surgery or open heart implantation of a replacement heart valve. See e.g., U.S. Pat. No. 4,106,129 (Carpentier), for a procedure that is highly invasive, fraught with patient risks, and requiring not only an extended hospitalization but also a highly painful recovery period.

Less invasive methods and devices for replacing a dysfunctional heart valve are also known and involve percutaneous access and catheter-facilitated delivery of the replacement valve. Most of these solutions involve a replacement heart valve attached to a structural support such as a stent, commonly known in the art, or other form of wire network designed to expand upon release from a delivery catheter. See, e.g., U.S. Pat. No. 3,657,744 (Ersek); U.S. Pat. No. 5,411,552 (Andersen). The self-expansion variants of the supporting stent assist in positioning the valve, and holding the expanded device in position, within the subject heart chamber or vessel. This self-expanded form also presents problems when, as is often the case, the device is not properly positioned in the first positioning attempt and, therefore, must be recaptured and positionally adjusted. This recapturing process in the case of a fully, or even partially, expanded device requires re-collapsing the device to a point that allows the operator to retract the collapsed device back into a delivery sheath or catheter, adjust the inbound position for the device and then re-expand to the proper position by redeploying the positionally adjusted device distally out of the delivery sheath or catheter. Collapsing the already expanded device is difficult because the expanded stent or wire network is generally designed to achieve the expanded state which also resists contractive or collapsing forces.

Besides the open heart surgical approach discussed above, gaining access to the valve of interest is achieved percutaneously via one of at least the following known access and delivery routes: femoral access, venous access, trans-apical, trans-aortic, trans-septal, trans-atrial, retrograde from the aorta delivery techniques.

Generally, the art is focused on systems and methods that, using one of the above-described known access routes, allow a partial delivery of the collapsed valve device, wherein one end of the device is released from a delivery sheath or catheter and expanded for an initial positioning followed by full release and expansion when proper positioning is achieved. See, e.g., U.S. Pat. No. 8,852,271 (Murray, III); U.S. Pat. No. 8,747,459 (Nguyen); U.S. Pat. No. 8,814,931 (Wang); U.S. Pat. No. 9,402,720 (Richter); U.S. Pat. No. 8,986,372 (Murray, III); and U.S. Pat. No. 9,277,991 (Salahieh); and U.S. Pat. Pub. Nos. 2015/0272731 (Racchini); and 2016/0235531 (Ciobanu).

However, known delivery systems, devices and methods still suffer from significant flaws in delivery methodology including, inter alia, positioning and recapture capability and efficiency.

In addition, known "replacement" heart valves are intended for full replacement of the native heart valve. Therefore, these replacement heart valves physically engage the annular throat and/or valve leaflets, thereby eliminating all remaining functionality of the native valve and making the patient completely reliant on the replacement valve. Generally speaking, it is a preferred solution that maintains and/or retains the native function of a heart valve, thus supplementation of the valve is preferred rather than full replacement. Obviously, there will be cases when native valve has either lost virtually complete functionality before the interventional implantation procedure, or the native valve continues to lose functionality after the implantation procedure. The preferred solution is delivery and implantation of a valve device that will function both as an adjunctive and/or supplementary functional valve as well as be fully capable of replacing the native function of a valve that has lost most or all of its functionality. However, the inventive solutions described infra will apply generally to all types and forms of heart valve devices, unless otherwise specified.

Further, known solutions for, e.g., the mitral valve replacement systems, devices and methods require 2-chamber solutions, i.e., there is involvement and engagement of the implanted replacement valve device in the left atrium and the left ventricle. Generally, these solutions include a radially expanding stent in the left atrium, with anchoring or tethering (disposed downward through the native annulus or annular throat) connected from the stent device down through the annular throat, with the sub-annular surface within the left ventricle, the left ventricular chordae tendineae and even into the left ventricle wall surface(s). See, e.g., the MitraClip® marketed by the Abbott Group and currently the only US approved repair device. With the MitraClip® a catheter containing the MitraClip® is inserted into the femoral vein. The device enters the heart through the inferior vena cava to the right atrium and delivered transseptally. The MitraClip® passes through the annulus into the left ventricle and sits below the leaflets, clipping the leaflets to decrease regurgitation.

Such 2-chamber and native annular solutions are unnecessary bulky and therefore more difficult to deliver and to position/recapture/reposition from a strictly structural perspective. Further, the 2-chamber solutions present difficulties in terms of making the ventricular anchoring and/or tethering connections required to hold position. Moreover, these solutions interfere with the native valve functionality as described above because the device portions that are disposed within the left ventricle must be routed through the native annulus and/or annular throat and native mitral valve, thereby disrupting any remaining coaptation capability of the native leaflets. In addition, the 2-chamber solutions generally require an invasive anchoring of some of the native tissue, resulting in unnecessary trauma and potential complication.

It will be further recognized that the 2-chamber mitral valve solutions require sub-annular and/or ventricular engagement with anchors, tethers and the like precisely because the atrial portion of the device fails to adequately anchor itself to the atrial chamber and/or upper portion of the annulus. Again, some of the embodiments, or portions thereof, described herein are readily applicable to single or 2-chamber solutions, unless otherwise indicated.

Finally, known prosthetic cardiac valves consist of two or three leaflets that are arranged to act as a one-way valve, permitting fluid flow therethrough in the antegrade direction while preventing retrograde flow. The mitral valve is located retrosternally at the fourth costal cartilage, consisting of an anterior and posterior leaflet, chordae tendinae, papillary muscles, ventricular wall and annulus connected to the atria. Each leaflet is supported by chordae tendinae that are attached to papillary muscles which become taut with each ventricular contraction preserving valvular competence. Both the anterior and posterior leaflets of the valve are attached via primary, secondary and tertiary chordae to both the antero-lateral and posterio-medial papillary muscles. A disruption in either papillary muscle in the setting of myocardial injury, can result in dysfunction of either the anterior or posterior leaflet of the mitral valve. Other mechanisms may result in failure of one, or both of the mitral leaflets. In the case of a single leaflet failure, the regurgitation may take the form of a non-central, eccentric jet of blood back into the left atrium. Other leaflet failures may comprise a more centralized regurgitation jet. Known prosthetic valve replacements generally comprise leaflets which are arranged to mimic the native valve structure, which may over time become susceptible to similar regurgitation outcomes.

Various embodiments of the present invention address these, inter alia, issues.

BRIEF DESCRIPTION OF THE SEVERAL VIEWS OF THE DRAWINGS

FIG. 1A illustrates a side view of one embodiment of the present invention.

FIG. 1B illustrates a bottom cutaway view of one embodiment of the present invention.

FIG. 2A illustrates a cutaway bottom view of one embodiment of the present invention.

FIG. 2B illustrates a cutaway bottom view of one embodiment of the present invention.

FIG. 2C illustrates a cutaway bottom view of one embodiment of the present invention.

DETAILED DESCRIPTION OF THE INVENTION

Figure 3:
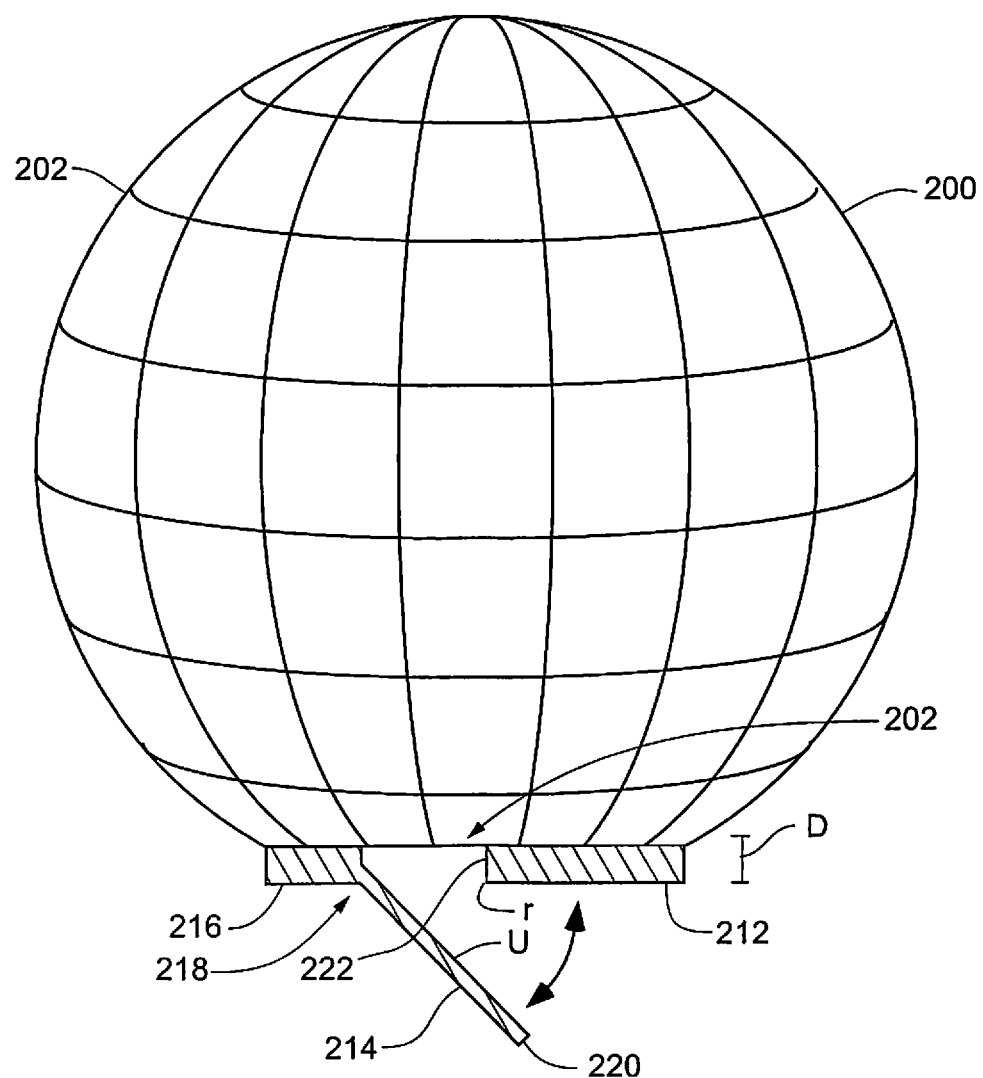
FIG. 3 illustrates a side view of one embodiment of the present invention.

FIGS. 1A and 1B provides an exemplary expanded prosthetic valve device 100 adapted for implantation within a heart chamber, e.g., the left atrium. An anchoring portion 102 is shown with a wire, e.g., a stent, construction that may be open, or at least partially open, when expanded within an exemplary left atrium. Anchoring portion 102 may be hollow and may provide a flow channel, shown in dashed lines at 103 in FIG. 1A, therethrough for blood flowing into the open wire construction of the anchoring portion 102 from the left pulmonary veins L into the left atrium where the device 100 is expanded and positioned for implantation. A lower section of anchoring portion 102, that is the section of the anchoring portion 102 that is located below the incoming blood flow points at the left pulmonary veins L, may be covered by fabric and/or tissue, either on the luminal side, the abluminal side, or on both the luminal and abluminal sides of the anchoring portion 102 to help channel the incoming blood flow into the flow channel 103 and to prevent paravalvular leakage.

The flow channel in FIGS. 1A and 1B terminates at a lower edge 104 of the anchoring portion with an exemplary prosthetic leaflet 106 hingedly attached thereto. As seen in FIG. 1B, the lower edge 104 may comprise a generally circular profile, though other shapes are within the scope of the present invention. Particularly, the undeformed expanded profile of the anchoring portion 102 and, in some cases, of the lower edge 104, may differ from a deformed expanded profile of anchoring portion 102 and lower edge 104 when the device 100 expands against atrial walls and the upper surface of the annulus. The embodiment illustrated in FIG. 1B comprises a single support wire, though a thicker configuration, e.g., a sewing ring, may also be provided. As the skilled artisan will readily recognize, lower edge 104 comprises a structure that allows a hinged or flexing connection with the single prosthetic leaflet 106.

As shown in FIGS. 2A and 2B, a single prosthetic leaflet 106 may comprise a perimeter 108 and a leaflet attachment zone 110 located along a portion of the perimeter 108. Thus, leaflet 106 may be connected with the lower edge 104 of the anchoring structure 102 or may be a separate structure that is attached or connected with the lower edge 104 of anchoring portion 102. Perimeter 108 in these leaflets 106 comprise a width, and in some cases a thickness, that may be formed of a material that differs from the material of the inner region 105 to facilitate attachment to the lower edge 104 of anchoring portion 102. In some embodiments, leaflet 106 may comprise a single material throughout as in FIG. 2C, wherein the perimeter 108 (shown in dashed lines) may comprise the same material as the inner region 105, though perimeter 108 may comprise a reinforced, e.g., double layer or folded layer of material.

In addition, the leaflet 106 may comprise a circular or a geometric, e.g., hexagonal, outer profile, see e.g. FIGS. 2A and 2B. These are simply exemplary shapes, all other shapes are within the scope of the present invention, so long as the leaflet 106 covers the opening defined by the lower edge 104 of the anchoring portion 102. Accordingly, lower edge 104 may be shaped with a variety of shapes, e.g., circular, semi-circular, when either expanded and deformed or expanded and undeformed. Any shape for lower edge 104 of the anchoring portion 102 is within the scope of the present invention, so long as the leaflet 106 is sized and shaped to cover the opening defined by lower edge 104.

The attachment mechanism between the valve leaflet 106 and support structure's leaflet attachment zone 110 may be seen with exemplary connection methods, and leaflet 106 structures, in FIGS. 2A-2C. FIG. 2 illustrates a series of connecting points which may be sutures or some other equivalent connective structure and that covers part of the outer surface of an exemplary circular valve leaflet such that the valve leaflet may swing open and closed using the connecting points as a hinge point. FIG. 3 illustrates an exemplary hexagonal valve leaflet with a series of connecting points within a leaflet attachment zone along one side of the hexagonal valve leaflet. Other shapes besides the circular and hexagonal valve leaflets shown here, e.g., oval, square, rectangle, pentagon, octagon, polygon, etc., are now readily recognized by the skilled artisan and within the scope of the present invention. Moreover, the connecting points within the leaflet attachment zone 110 may comprise a structure that consists of one or more unbroken connectors, including but not limited to adhesive or gluing, continuous stitching, integrally forming the valve leaflet 106 with the anchoring structure 102, preferably with the lower edge 104 thereof, and/or clamping the valve along the leaflet attachment zone 110 to the anchoring structure, again preferably with the lower edge 104 thereof.

The prosthetic valve leaflet 106 thus acts like a hinged door in that it may rotate or swing between a closed position and an open position relative to the lower edge 104 of anchoring portion 102 with a portion of the leaflet 106 secured to a portion of the lower edge 104 of the anchoring portion 102 along the leaflet attachment zone 110 by, e.g., a plurality of sutures or the equivalent.

The closed position results in a temporary engagement and sealing of an outer portion of the upper surface of the valve leaflet against the bottom surface of the lower edge 104 of the structure 102, the prosthetic valve leaflet 106 being of a size and shape to cover the opening defined by lower edge 104 of anchoring portion 102, thereby preventing retrograde blood flow therethrough. The open position disengages the upper surface of the valve leaflet 106 from the bottom surface of the lower edge 104 to allow blood to flow therethrough.

A preferred positioning within the left atrium may comprise positioning at least a portion of the bottom surface of the anchoring structure 102 on at least a portion of the upper annular surface of the left atrium as in FIG. 1A. However, in other embodiments, the prosthetic leaflet 106 may be positioned above, or spaced away from, the native valve leaflets so that physical interference does not occur between the prosthetic valve leaflet 106 and the native leaflets and to maintain the remaining functionality of the native leaflets. In this case, device 100 will function to supplement the native leaflet functionality and, if and when needed, will begin to take over progressively more functionality as the native leaflets deteriorate. Eventually, the device 100 will function to replace all, or virtually all of the native leaflet functionality. The result is a device 100 that adapts to progressively assume the functionality of the native leaflets as they deteriorate, from supplementation through full replacement.

Thus, in certain embodiments, the valve leaflet 106 may be elevated or spaced above the native annular surface so that at least a portion of the valve leaflet 106 in the opened position is also elevated or spaced above at least the upper annular surface. In other cases at least a portion of the valve leaflet 106 in the open position may be disposed above the native valve leaflets so as to not physically interfere with them, or minimize physical interaction therewith. In these embodiments, the prosthetic leaflet may serve at least a supplementary function to the native leaflet function.

In other cases, a support for the prosthetic leaflet may be disposed within the native annulus or annular throat, effectively pinning the native leaflets and requiring the inventive valve leaflet to completely replace the native leaflet function.

In the embodiments with the support structure and valve leaflets are elevated or spaced above at least the native leaflets and/or the upper annular surface, the prosthetic leaflet will open in response to increased fluid pressure in the left atrium and allow blood to flow down to the spaced away native leaflets which also open, enabling blood flow to the left ventricle. The native leaflets will then close to the extent possible in response to increased fluid pressure in the left ventricle and, in response to the regurgitation pressure in the space between the native leaflets and the prosthetic leaflet, the prosthetic leaflet will then close, preventing retrograde blood flow into the left atrium.

In the event of eventual complete native leaflet failure, the prosthetic leaflet will completely handle and manage the blood flow between the left atrium and ventricle.

It is part of the present invention to orient the prosthetic leaflet 106 opening and leaflet attachment zone 110 to optimize the supplemental and/or replacement function, for example and without limitation in the case where a single native leaflet is dysfunctional and a result is an eccentric, non-central regurgitation jet. The new valve leaflet 106 may be oriented, e.g., so that the eccentric regurgitation jet is focused at the bottom surface of a distal end (away from the leaflet attachment zone 110) of the valve leaflet 106, in the middle of the valve leaflet (as measured relative to the distal end and the leaflet attachment zone 110), or closer to the leaflet attachment zone 110, or at points between the distal end and midpoint, or between the midpoint and the leaflet attachment zone 110 in order to maximize closure efficiency of the prosthetic leaflet 106.

In addition, the exit flow direction and/or position may be affected by the positioning/orientation of the leaflet attachment zone 110 as well as the degree to which the valve leaflet 106 is allowed to open, so as to direct the blood flow to an optimal location on the native valve leaflets. A fully opened prosthetic valve leaflet 106 may comprise opening to a position that is approximately 90 degrees from its closed position. Opening positions for the prosthetic valve leaflet 106 of less than 90 degrees from the closed position will channel the blood flow in a direction along the length of the opened leaflet 106 toward a target on the native leaflets. Thus, as seen in FIG. 1A, leaflet 106 may be fully opened to approximately a 45 degree angle relative to its closed position against lower edge 104 of the anchoring structure 102. This configuration will direct the incoming blood flow 103 generally along the same direction as the open position of the leaflet 106. Therefore, not only is the opening angle of the leaflet 106 important, but so is the orientation of the anchoring structure 102 on expansion which will dictate the location of the leaflet attachment zone 110 which, in turn, dictates the location of the opening leaflet 106 and resultant blood flow therealong. Another variable relative to locating the blood flow along the opened leaflet 106 is the distance of the distal end of the opened leaflet 106 from the target region in the native leaflets. It will be obvious now that, in order to optimize delivery location targeting of the blood flow moving across the opened leaflet 106, that the following parameters will require systemic optimization: the maximum opened angle at the open position for the prosthetic valve leaflet 106; the orientation of the distal end of the prosthetic valve leaflet 106 when the device 100 is expanded; and the distance, height or spacing of the distal end of the prosthetic valve leaflet 106 from the targeted location on the native valve leaflets. Optimization of this system allows consistent targeting of an area of the native valve leaflets for the blood flow moving through the prosthetic valve device 100.

FIG. 3 illustrates an alternate embodiment for a prosthetic valve device 200 that is similar to the prosthetic valve device 100 discussed above in certain respects. Accordingly, the anchoring structure 202 has the same or similar features and characteristics as the anchoring structure 102 of device 100, e.g., a collapsible and expandable structure that may comprise a stent-like structure with open cells.

The valve support structure 204, as illustrated in FIG. 3 comprises two basic elements arranged on opposing sides of a lower opening 201 defined by the anchoring structure 202. A first fixed base side 212 that may be more stiff than, or of similar stiffness to, the structure comprising the dome and extends a distance D away from the lower opening 201 and may comprise an expanded and collapsed configurations. Positioned across the lower opening 201 from the first fixed base side 212 of valve support 204 is a moveable, rotatable valve member 214 that is connected to, or operatively engaged with, or attached to, or integrally formed with, a second fixed base side 216 that may be of similar stiffness, or different stiffness, as the first fixed base side 212 and may also comprise expanded and collapsed configurations. The rotatable valve member 214 may be formed of a tissue or fabric that is less stiff than the second fixed base side 216 and may comprise sizes and shapes as describe above regarding the prosthetic valve of FIG. 1A.

Figure 4:
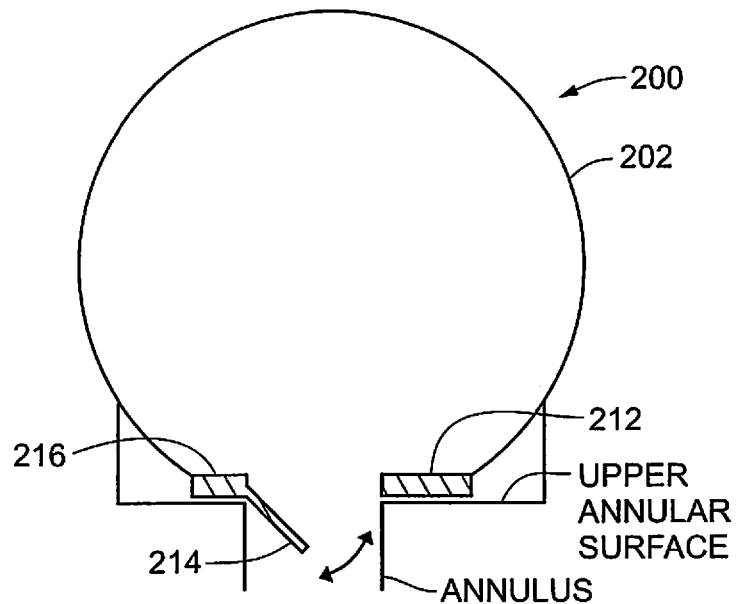
FIG. 4 illustrates a side view of one embodiment of the present invention.

In either case, there may be a region or point of flexion 218 comprising a decreased stiffness and/or increased flexibility that allows the rotatable valve 214 to move upward to engage the first fixed base side 212 when the valve 214 is in a closed position and to move downward away from the first fixed base side 212 when the valve member 214 is in an open position. Fluid flow force generated by blood flow from the left atrium will be sufficient to push the rotatable valve member 214 to an open position as shown in FIG. 4, thereby enabling fluid communication of the atrial blood with the left ventricle. When the atrial to ventricular blood flow is complete and regurgitation forces are present, those forces cause the valve member 214 to rotate up and close against the first fixed base side 212, preventing regurgitant blood from flowing into the interior of the anchoring structure 202.

In a preferred embodiment, the rotatable valve member 214 may be biased in the closed position, pressed with a predetermined amount of biasing force against the first fixed base side 212, so that the closed position for valve member 214 is the biased position. This requires that the blood flow from the atrium exert sufficient force to overcome the biasing force of the valve member 214 against first fixed base side 212 to cause the valve member 214 to rotate into an open position. The valve member 214 may, when closed and as shown, overlap with the inner edge of the first fixed base side 212, so that the upper (upstream) side U of valve member 214 engages the inner edge I of the first fixed base side 212 in the closed position. Alternatively, the distal end 220 of valve member 214 may fit against the distal end 220 of the first base fixed side 212 to provide a generally sealed closure.

Figure 5:
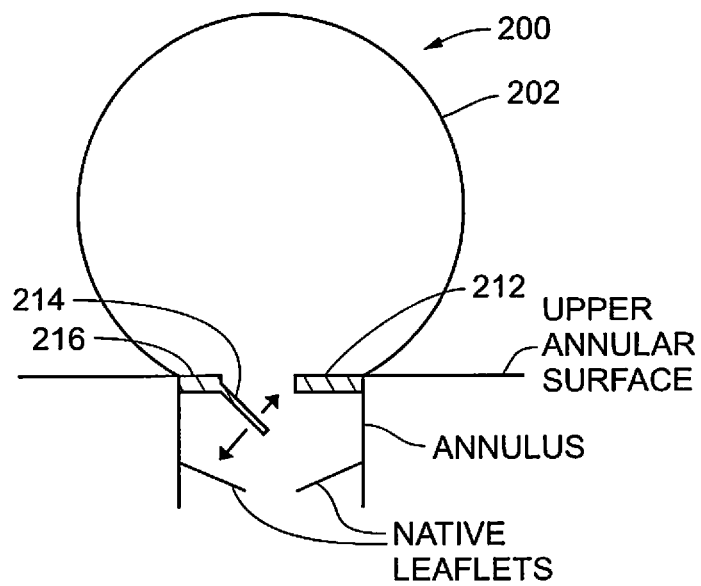
FIG. 5 illustrates a side view of one embodiment of the present invention.

The device of FIG. 3 may be positioned within the left atrium so that the first and second sides of the base 212, 216 rest upon the upper annular surface with the prosthetic rotatable leaflet 214 positioned over the annulus as in FIG. 4 so that the distal end 220 of leaflet 214 may extend into the annulus when in an open position. Alternatively, the distance D of extension of the first and second sides of the base 212, 216 may be used to locate and/or position the device 200 slightly within the annulus, with the first and second sides 212, 216 of the base extending downward (downstream) into the annulus as in FIG. 5.

As described in connection with device 100 above, the location of blood flow through device 200 and across rotatable leaflet 214 may be optimized as a system by configuring the degree of angle of maximum opening for leaflet 214, the rotational location of the leaflet 214, specifically the end of the leaflet located away from the point of flexion 218, and the distance or spacing of the end of the leaflet located furthermost from the point of flexion 218 when opened in the open position, i.e., maximum degree of opening. In addition, system elements that may be optimized for locating the blood flow onto native leaflets comprise the distance of extension of the first base side 212 over the annulus. In some cases, the first base side 212 may not extend over the annulus, instead the distal end 222 of the first base side 212 may be coextensive with an edge of the annulus, see e.g., FIG. 4. In other cases, the distal end 222 of the first base side 212 may extend a distance beyond the annular edge and, therefore, over the annulus the same distance.

Figure 6:
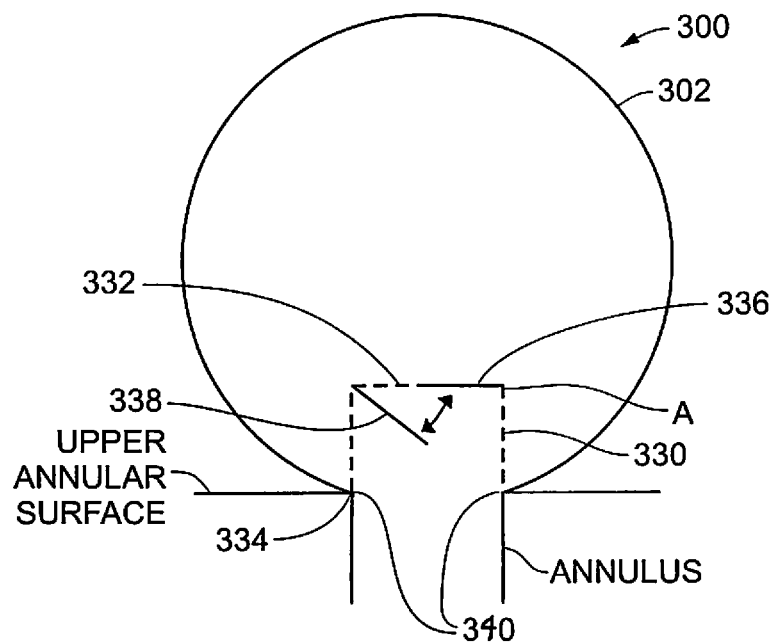
FIG. 6 illustrates a side view of one embodiment of the present invention.

Further, a modified embodiment of the device 200 of FIG. 3 may locate the prosthetic rotatable leaflet 214 at a position that is located above the native annular surface, i.e., in a super annular position, that does not result in any physical touching of the native valve leaflets. Thus, as shown in FIG. 6, device 300 comprises an anchoring support 302 and a valve support 330. The valve support comprises an inflow end 332 and an outflow end 334 and defines a flow channel therebetween. A first base side 336 may be attached along the flow channel of the valve support 330 and a prosthetic leaflet 338 attached at a position along the flow channel of the valve support 330 that enables engagement of the first base side 336 by the prosthetic leaflet 338 when in a closed position. Thus, the prosthetic leaflet 338 and first base side 336 may be positioned and spaced above the upper annular surface at exemplary position A, though it is understood that the prosthetic leaflet 338 and first base side 336 may be positioned at any point along the flow channel of the valve support 330. Stated differently, the prosthetic leaflet 338 and first base side 336 may be positioned at any point between the inflow and outflow ends 332, 334 of the valve support 330 including, but not limited to, a location that is coplanar with the upper annular surface.

It is understood that first base side 336 may comprise a very small lip structure to stop the upward rotation of the valve 338 and achieve the closed position to prevent regurgitation. The lip structure may surround valve support 338 to form a temporary seal between lip structure/first base side 336 and the closed prosthetic leaflet 338.

Valve support 330 may be a cylindrical structure as illustrated or may comprise a section of a cone, with increasing distance between the cone sides moving from the inflow end to the outflow end of the valve support 330. Alternatively, the valve support 330 may comprise a conical section with decreasing distance between the cone sides moving from the inflow end 332 to the outflow end 334 of the valve support 330. Other configurations for the valve support 330 may present themselves to the skilled artisan, each being within the scope of the present invention.

Figure 7:
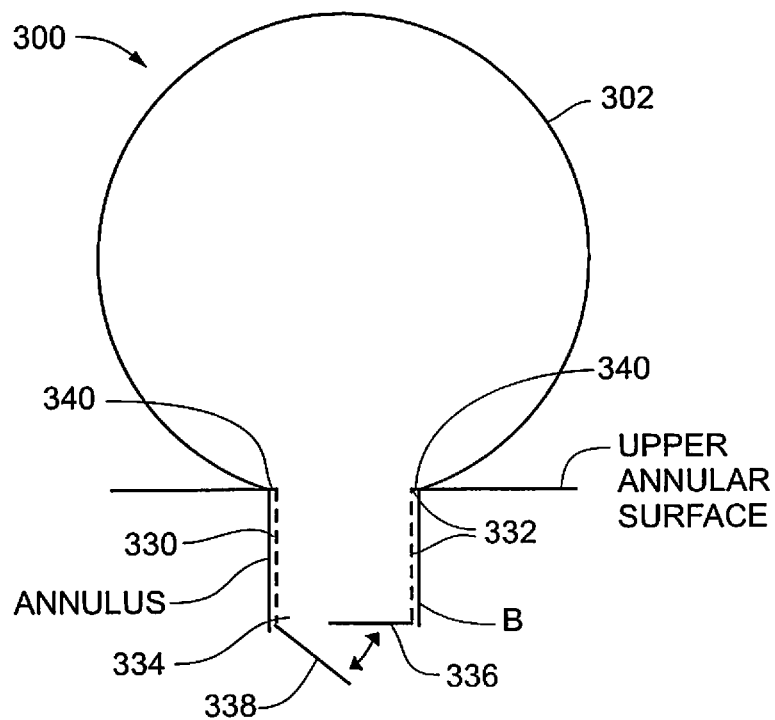
FIG. 7 illustrates a side view of one embodiment of the present invention.

Alternatively, as in FIG. 7, the valve support 330, prosthetic leaflet 338 and fixed first side 336 may be positioned as extended downstream into the native annulus as indicated by position B. The length of extension of the valve support 330 relative to the lower opening of the anchoring structure 302 into the native annulus, dictates the position of the prosthetic valve leaflet 338 relative to the native leaflets. In some embodiments, the valve support 330 terminates at a point above the native leaflets, while in other cases the valve support 330 may extend to and perhaps beyond the native leaflets within the annulus, thereby pinning the native leaflets against the annulus. In all cases, the location of the prosthetic leaflet 338 and fixed first side 336 may be positioned at any point within the valve support 330 between the inflow end 332 and the outflow end 334.

Valve support 330 in FIGS. 6 and 7 may comprise a separate structure that is mechanically connected with the lower opening of the anchoring structure 302.

Alternatively, and preferably, the anchoring structure 302 comprises an expandable and collapsible transition section 340 whereby the anchoring structure turns radially inwardly to form the valve support 330. In this latter case, the valve support 330, transition section 340, and anchoring structure 302 comprise a unitary structure that may comprise different characteristics in each of the valve support 330, transition section 340 and anchoring structure 302. For example, stent cell sizes and/or arrangements may differ between the aforementioned device elements 330, 340 and/or 302. But, in this embodiment, the unitary construction allows the device of FIG. 6, in some cases, to be turned inside out, by pulling the valve support 330 outwardly and radially away from the anchoring structure. For illustrative purposes, such a turned-out device when expanded would resemble that shown in FIG. 7. This capability is highly advantageous during transition of the collapsed device through a delivery catheter to the heart chamber as the collapsed turned-out device of, e.g., FIG. 7, comprises only two layers as opposed to the non-turned-out device of FIG. 6 which, in the region of the valve support 330 comprises four layers and is, therefore, two layers thicker.

In some cases, the device of FIG. 7 is desired in the expanded configuration to position the valve support 330 within the annulus. In other cases, the device of FIG. 6 is desired for positioning the valve support 330 radially within the anchoring support 302 and for allowing location of the prosthetic valve 338 at, or above, the annular surface.

If the device of FIG. 6 is turned-out as shown in FIG. 7 for example, to facilitate delivery, the device 300 will be reconfigured after release from the distal end of the delivery catheter by pulling the valve support 330 radially back into the anchoring support 302 interior space to achieve the structure of the exemplary device of FIG. 6.

Thus, in the unitary structure case, the embodiment of FIG. 6 comprises the inflow end 332 of the valve support 330 is located at a position that is radially within the interior of anchoring structure 302 and the transition section 340 forms the outflow end 334 of the valve support 302, wherein the inflow end 332 of valve support 330 is spaced radially inward and away from the transition section 340. In FIG. 7, the inflow end 332 of the valve support 330 is defined by and substantially coextensive with the transition section 340, with the outflow end 334 of the valve support 330 extending radially outwardly away from the transition section 340.

Figure 8:
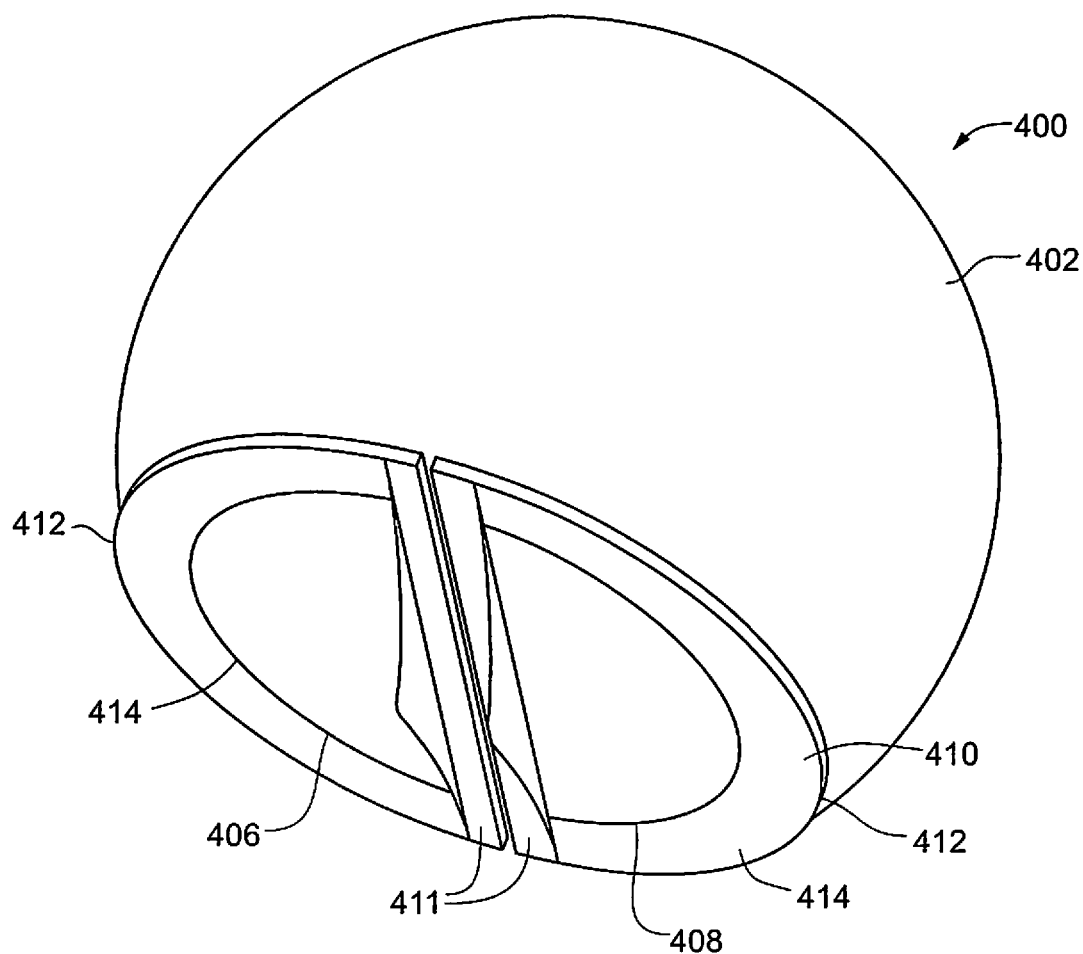
FIG. 8 illustrates a bottom perspective view of one embodiment of the present invention.
Figure 9:
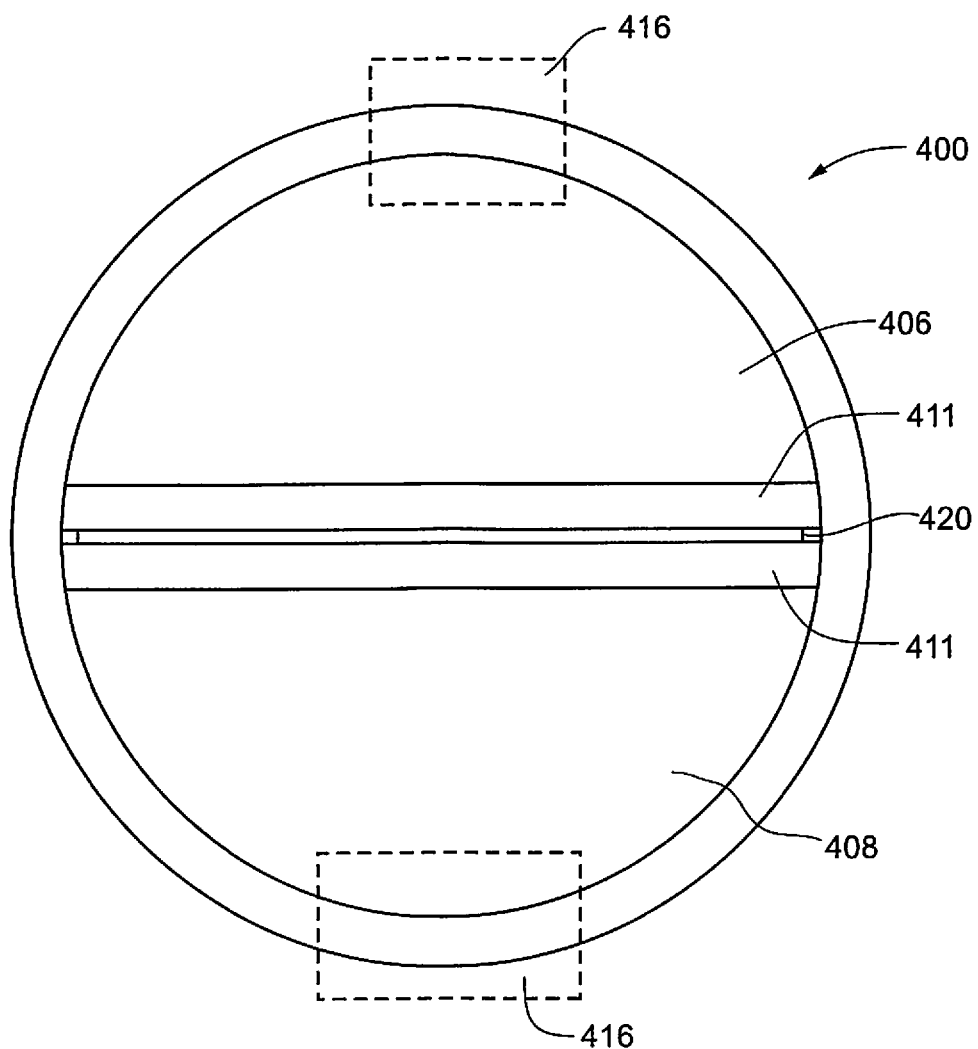
FIG. 9 illustrates a bottom view of one embodiment of the present invention.
Figure 10:
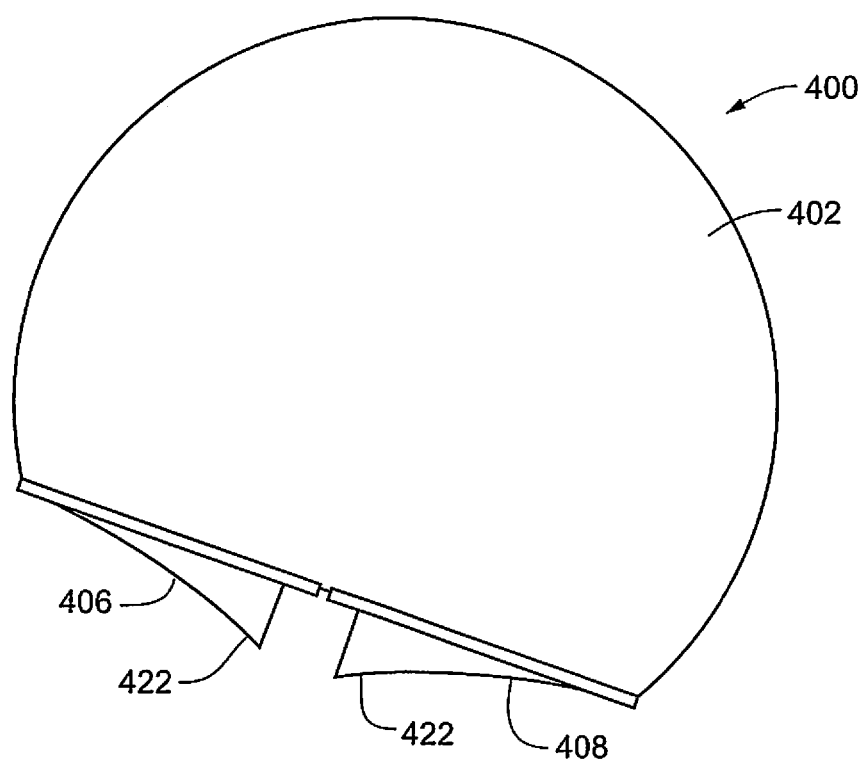
FIG. 10 illustrates a side view of one embodiment of the present invention.

Turning now to FIGS. 8-10, a two-door valved device 400 is illustrated and comprising an anchoring section 402 similar to the device 100, 200, 300 described above. Valve support section 404 comprises a first valve flap 406 and a second valve flap 408 that open and close against a lower opening 410 defined by anchoring section 402 and adapted to hingedly engage first and second valve flaps 406, 408.

Each of the first and second valve flaps 406, 408 may comprise a relatively stiff or rigid outer frame 412 in the general shape of a half circle, or other curvilinear form, and comprise a material on the inner portion 414 of the outer frame, e.g., tissue or fabric or other material with a central straight or linear section 411 connecting the two ends of the half-circle-shaped outer frame 412. At least one flexion, or hinging, region 416 is provided to bias the first and second valve flaps 406, 408 in the closed position (as shown) and to allow opening of the first and second valve flaps 406, 408 when the biasing force is overcome by blood flow pressure force as described above.

In this embodiment, the first and second valve flaps 406, 408 may comprise a sealing engagement together at the central straight or linear section 411 of the outer frame 412. This may be a total or partial seal and may be supplemented by a biocompatible and flexible gasket or liner 420 on one or both of the central straight or linear section 411 of the outer frame 412 to ensure sealing when the flaps close together.

An alternate embodiment shown in FIG. 10 may comprise the first and second valve flaps 406, 408 comprising a sail feature 422 attached at one end to the first and second valve flaps 406, 408 and free to move at the opposing end and comprising material having a generally downwardly curving profile, when engaged by blood flow from below, may catch upwardly flowing fluid, similar to the way sails catching wind, to flex and aid in generating upward force to close the flaps 406, 408 more efficiently and quickly to prevent regurgitation.

Moreover, it is contemplated that any prosthetic valve devices described herein, including for example the anchoring portions as described herein, as well as the prosthetic valve leaflets or prosthetic valve flaps and/or valve support structures as described herein may comprise a releasable amount of a therapeutic agent thereon for localized application to the heart chamber tissue and/or to the native valves, annulus or other structure. Further, the therapeutic agent disposed in or on the prosthetic device may target blood vessels, bodily conduits, or specific organs contacted by the circulatory system to treat, and/or prevent, a bodily disorder and/or accelerate a desired bodily response, e.g., and without limitation endotheliazation.

For the purposes of the present invention, the following terms and definitions apply:

"Bodily disorder" refers to any condition that adversely affects the function of the body.

The term "treatment" includes prevention, reduction, delay, stabilization, and/or elimination of a bodily disorder, e.g., a failing cardiac valve or a vascular disorder. In certain embodiments, treatment comprises repairing damage cause by the bodily, e.g., valvular or vascular, disorder and/or intervention of same, including but not limited to mechanical intervention.

A "therapeutic agent" comprises any substance capable of exerting an effect including, but not limited to therapeutic, prophylactic or diagnostic. Thus, therapeutic agents may comprise anti-inflammatories, anti-infectives, analgesics, anti-proliferatives, and the like including but not limited to antirestenosis drugs and therapeutic agents that accelerate endothelial coverage and endotheliazation, including but certainly not limited to a therapy stent marketed by Orbus-Neich™ that is designed to repair vessel injury and regenerate the endothelium, to foster vessel healing achieved by accelerating endothelial coverage and controlling neo-intimal proliferation with a combination of endothelial progenitor cell capture and a sirolimus drug elution.

Therapeutic agent as used and defined herein further comprises mammalian stem cells. Therapeutic agent as used herein further includes other drugs, genetic materials and biological materials. The genetic materials mean DNA or RNA, including, without limitation, of DNA/RNA encoding a useful protein, intended to be inserted into a human body including viral vectors and non-viral vectors. Viral vectors include adenoviruses, gutted adenoviruses, adeno-associated virus, retroviruses, alpha virus, lentiviruses, herpes simplex virus, ex vivo modified cells (e.g., stem cells, fibroblasts, myoblasts, satellite cells, pericytes, cardiomyocytes, skeletal myocytes, macrophage), replication competent viruses, and hybrid vectors. Non-viral vectors include artificial chromosomes and mini-chromosomes, plasmid DNA vectors, cationic polymers, graft copolymers, neutral polymers PVP, SP1017, lipids or lipoplexes, nanoparticles and microparticles with and without targeting sequences such as the protein transduction domain (PTD). The biological materials include cells, yeasts, bacteria, proteins, peptides, cytokines and hormones. Examples for peptides and proteins include growth factors (FGF, FGF-1, FGF-2, VEGF, Endotherial Mitogenic Growth Factors, and epidermal growth factors, transforming growth factor .alpha. and .beta., platelet derived endothelial growth factor, platelet derived growth factor, tumor necrosis factor .alpha., hepatocyte growth factor and insulin like growth factor), transcription factors, proteinkinases, CD inhibitors, thymidine kinase, and bone morphogenic proteins. These dimeric proteins can be provided as homodimers, heterodimers, or combinations thereof, alone or together with other molecules.

Therapeutic agents further include cells that may be of human origin (autologous or allogeneic) or from an animal source (xenogeneic), genetically engineered, if desired, to deliver proteins of interest at the transplant site. Cells within the definition of therapeutic agents herein further include whole bone marrow, bone marrow derived mono-nuclear cells, progenitor cells (e.g., endothelial progenitor cells) stem cells (e.g., mesenchymal, hematopoietic, neuronal), pluripotent stem cells, fibroblasts, macrophage, and satellite cells.

Therapeutic agent also includes non-genetic substances, such as: anti-thrombogenic agents such as heparin, heparin derivatives, and urokinase; anti-proliferative agents such as enoxaprin, angiopeptin, or monoclonal antibodies capable of blocking smooth muscle cell proliferation, hirudin, and acetylsalicylic acid, amlodipine and doxazosin; anti-inflammatory agents such as glucocorticoids, betamethasone, dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, methotrexate, azathioprine, adriamycin and mutamycin; endostatin, angiostatin and thymidine kinase inhibitors, taxol and its analogs or derivatives; anesthetic agents such as lidocaine, bupivacaine, and ropivacaine; anti-coagulants such as heparin, antithrombin compounds, platelet receptor antagonists, anti-thrombin antibodies, anti-platelet receptor antibodies, aspirin, dipyridamole, protamine, hirudin, prostaglandin inhibitors, platelet inhibitors and tick antiplatelet peptides; vascular cell growth promoters such as growth factors, Vascular Endothelial Growth Factors, growth factor receptors, transcriptional activators, and translational promoters; vascular cell growth inhibitors such as antiproliferative agents, growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms; anti-oxidants, such as probucol; antibiotic agents, such as penicillin, cefoxitin, oxacillin, tobranycin angiogenic substances, such as acidic and basic fibroblast growth factors, estrogen including estradiol (E2), estriol (E3) and 17-Beta Estradiol; and drugs for heart failure, such as digoxin, beta-blockers, angiotensin-converting enzyme, inhibitors including captopril and enalopril. The biologically active material can be used with (a) biologically non-active material(s) including a solvent, a carrier or an excipient, such as sucrose acetate isobutyrate, ethanol, n-methyl pyrolidone, dimethyl sulfoxide, benzyl benzoate and benzyl acetate.

Further, "therapeutic agent" includes, in particular in a preferred therapeutic method of the present invention comprising the administration of at least one therapeutic agent to a procedurally traumatized, e.g., by an angioplasty or atherectomy procedure, mammalian vessel to inhibit restenosis. Preferably, the therapeutic agent is a cytoskeletal inhibitor or a smooth muscle inhibitor, including, for example, taxol and functional analogs, equivalents or derivatives thereof such as taxotere, paclitaxel, Abraxane™, Coroxane™ or a cytochalasin, such as cytochalasin B, cytochalasin C, cytochalasin A, cytochalasin D, or analogs or derivatives thereof.

Additional specific examples of "therapeutic agents" that may be applied to a bodily lumen using various embodiments of the present invention comprise, without limitation: L-Arginine; Adipose Cells; Genetically altered cells, e.g., seeding of autologous endothelial cells transfected with the beta-galactosidase gene upon an injured arterial surface; Erythromycin; Penicillin: Heparin; Aspirin; Hydrocortisone; Dexamethasone; Forskolin; GP IIb-IIIa inhibitors; Cyclohexane; Rho Kinase Inhibitors; Rapamycin; Histamine; Nitroglycerin; Vitamin E; Vitamin C; Stem Cells; Growth Hormones; Hirudin; Hirulog; Argatroban; Vapirprost; Prostacyclin; Dextran; Erythropoietin; Endothelial Growth Factor; Epidermal Growth Factor; Core Binding Factor A; Vascular Endothelial Growth Factor; Fibroblast Growth Factors; Thrombin; Thrombin inhibitor; and Glucosamine, among many other therapeutic substances.

The therapeutic agent delivery system of the present invention, i.e., the prosthetic valve device, may be used to apply the therapeutic agent to any surface of cardiac chambers, e.g., the left atrium, as well as cardiac chambers in fluid or operative communication with the left atrium, e.g., the left ventricle and/or annulus located therebetween. In addition, the delivery system may be used to deliver an effective amount of therapeutic agent(s) to a body lumen in fluid and/or operative communication with the left atrium and related circulatory system. Such body lumens include, inter alia, blood vessels, urinary tract, coronary vasculature, esophagus, trachea, colon, and biliary tract. The therapeutic agent(s) may be coated to some, or all, of the prosthetic valve device as in known in the art to enable a time-release of the therapeutic agent(s) to the target(s) within the patient's body and may be provided so as to enable administration and delivery of an effective dose of the therapeutic agent(s) to the target(s).

Delivery of the agent(s) may be achieved through pressured contact of the therapeutic agent(s) on or in the prosthetic valve device as it expands against the cardiac chamber when positioned, similar to a coated expandable intravascular balloon or stent. The therapeutic agent(s) will then diffuse into the tissue. Alternatively, the therapeutic agent(s) may be swept into the blood flow with delivery to other non-cardiac chamber targets, e.g., tissues, organs, lumens, etc., including but not limited to the dysfunctioning native valve structure including leaflets.

The description of the invention and its applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. A prosthetic mitral valve device adapted to anchor within a left atrium of a heart for supplementing and/or replacing function of dysfunctional native mitral valve leaflets disposed within an annulus located between the left atrium and a left ventricle of the heart, the device comprising:
   an expandable anchoring structure defining a lower opening;
   a first base side comprising a lower surface and operatively engaged with the expandable anchoring structure at the lower opening; and
   a second base side operatively engaged with the expandable anchoring structure at the lower opening and comprising a single prosthetic leaflet comprising an upper surface; wherein:
      the upper surface of the single prosthetic leaflet is adapted to directly engage the lower surface of the first base side in a closed position to cover the lower opening to prevent retrograde blood flow, resulting from the dysfunctional native mitral valve leaflets, through the lower opening; and
      the single prosthetic leaflet is adapted to rotate away from the first base side in an open position to allow blood to flow through the lower opening.

2. The device of claim 1, wherein, when the device is anchored within the left atrium, the first base side and the second base side are positioned on an upper annular surface within the left atrium and the single prosthetic leaflet is positioned over the annulus.

3. The device of claim 1, wherein the first base side and the second base side extend a distance away from the lower opening of the anchoring structure.

4. The device of claim 3, wherein the first base side and the second base side are adapted to fit within the annulus.

5. The device of claim 1, wherein the device, when anchored within the left atrium, is adapted to supplement function of dysfunctional native mitral valve leaflets.

6. The device of claim 5, wherein the device does not physically interact with the native mitral valve leaflets.

7. The device of claim 1, wherein the device, when anchored within the left atrium, is adapted to replace function of dysfunctional native mitral valve leaflets.

8. The device of claim 7, wherein the device does not physically interact with the native mitral valve leaflets.

9. The device of claim 5, wherein the device is adapted to progressively take over functionality from the dysfunctional native leaflets.

10. The device of claim 1, wherein the expandable anchoring structure comprises open cell stent construction.

11. The device of claim 1, wherein the single prosthetic leaflet is biased to the closed position.

12. The device of claim 1, wherein the single prosthetic leaflet comprises a flexion point adapted to allow the single prosthetic leaflet to move between the open position and the closed position.

13. The device of claim 4, wherein the first base side and second base side are adapted to locate and position the device within the annulus and left atrium.

* * * * *